(12) United States Patent
Lieber et al.

(10) Patent No.: US 7,619,290 B2
(45) Date of Patent: *Nov. 17, 2009

(54) NANOSENSORS

(75) Inventors: Charles M. Lieber, Lexington, MA (US); Hongkun Park, Lexington, MA (US); Qingqiao Wei, Corvallis, OR (US); Yi Cui, Sunnyvale, CA (US); Wenjie Liang, Oakland, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/038,794

(22) Filed: Feb. 27, 2008

(65) Prior Publication Data

US 2008/0211040 A1 Sep. 4, 2008

Related U.S. Application Data

(60) Continuation of application No. 11/582,167, filed on Oct. 17, 2006, now Pat. No. 7,385,267, which is a division of application No. 10/020,004, filed on Dec. 11, 2001, now Pat. No. 7,129,554.

(60) Provisional application No. 60/254,745, filed on Dec. 11, 2000, provisional application No. 60/292,035, filed on May 18, 2001.

(51) Int. Cl.
*H01L 27/14* (2006.01)
*H01L 29/82* (2006.01)
*H01L 29/84* (2006.01)

(52) U.S. Cl. .............................. 257/414; 257/E31.002; 257/E31.003; 977/762

(58) Field of Classification Search ................ 257/414, 257/E31.002, E31.003; 977/762
See application file for complete search history.

(56) References Cited

U.S. PATENT DOCUMENTS

| 3,873,359 | A | 3/1975 | Lando |
| 3,873,360 | A | 3/1975 | Lando |
| 3,900,614 | A | 8/1975 | Lando |
| 4,673,474 | A | 6/1987 | Ogawa |
| 4,939,556 | A | 7/1990 | Eguchi et al. |
| 5,023,139 | A | 6/1991 | Birnboim et al. |
| 5,089,545 | A | 2/1992 | Pol |

(Continued)

FOREIGN PATENT DOCUMENTS

CN 1110786 A 10/1995

(Continued)

OTHER PUBLICATIONS

Agarwal, R. et al., "Lasing in Single Cadmium Sulfide Nanowire Optical Cavities," *Nano Letters*, 2005, 5(5):917-920.

(Continued)

*Primary Examiner*—Victor A Mandala
(74) *Attorney, Agent, or Firm*—Wolf, Greenfield & Sacks, P.C.; Timothy J. Oyer

(57) ABSTRACT

Electrical devices comprised of nanowires are described, along with methods of their manufacture and use. The nanowires can be nanotubes and nanowires. The surface of the nanowires may be selectively functionalized. Nanodetector devices are described.

8 Claims, 17 Drawing Sheets

U.S. PATENT DOCUMENTS

| | | | |
|---|---|---|---|
| 5,252,835 A | 10/1993 | Lieber et al. | |
| 5,274,602 A | 12/1993 | Glenn | |
| 5,453,970 A | 9/1995 | Rust et al. | |
| 5,475,341 A | 12/1995 | Reed | |
| 5,512,131 A | 4/1996 | Kumar et al. | |
| 5,524,092 A | 6/1996 | Park | |
| 5,537,075 A | 7/1996 | Miyazaki | |
| 5,539,214 A * | 7/1996 | Lynch et al. | 257/15 |
| 5,581,091 A | 12/1996 | Moskovits et al. | |
| 5,589,692 A | 12/1996 | Reed | |
| 5,607,876 A | 3/1997 | Biegelsen et al. | |
| 5,620,850 A | 4/1997 | Bamdad et al. | |
| 5,640,343 A | 6/1997 | Gallagher et al. | |
| 5,726,524 A | 3/1998 | Debe | |
| 5,739,057 A | 4/1998 | Tiwari et al. | |
| 5,747,180 A | 5/1998 | Miller et al. | |
| 5,751,156 A | 5/1998 | Muller et al. | |
| 5,776,748 A | 7/1998 | Singhvi et al. | |
| 5,824,470 A | 10/1998 | Baldeshwieler et al. | |
| 5,830,538 A | 11/1998 | Gates et al. | |
| 5,840,435 A | 11/1998 | Lieber et al. | |
| 5,847,565 A | 12/1998 | Narayanan | |
| 5,858,862 A * | 1/1999 | Westwater et al. | 438/503 |
| 5,864,823 A | 1/1999 | Levitan | |
| 5,866,434 A | 2/1999 | Massey | |
| 5,897,945 A | 4/1999 | Lieber et al. | |
| 5,900,160 A | 5/1999 | Whitesides et al. | |
| 5,903,010 A | 5/1999 | Flory et al. | |
| 5,908,692 A | 6/1999 | Hamers et al. | |
| 5,916,642 A | 6/1999 | Chang | |
| 5,942,443 A | 8/1999 | Parce et al. | |
| 5,997,832 A | 12/1999 | Lieber et al. | |
| 6,004,444 A | 12/1999 | Aksay | |
| 6,036,774 A | 3/2000 | Lieber et al. | |
| 6,038,060 A | 3/2000 | Crowley | |
| 6,060,121 A | 5/2000 | Hidber et al. | |
| 6,060,724 A | 5/2000 | Flory et al. | |
| 6,069,380 A | 5/2000 | Chou et al. | |
| 6,123,819 A * | 9/2000 | Peeters | 204/452 |
| 6,128,214 A | 10/2000 | Kuekes et al. | |
| 6,143,184 A | 11/2000 | Martin et al. | |
| 6,149,819 A | 11/2000 | Martin et al. | |
| 6,159,742 A | 12/2000 | Lieber et al. | |
| 6,180,239 B1 | 1/2001 | Whitesides et al. | |
| 6,187,165 B1 | 2/2001 | Chien et al. | |
| 6,190,634 B1 | 2/2001 | Lieber et al. | |
| 6,203,864 B1 | 3/2001 | Zhang et al. | |
| 6,207,392 B1 | 3/2001 | Weiss et al. | |
| 6,211,464 B1 | 4/2001 | Mochizuki et al. | |
| 6,231,744 B1 | 5/2001 | Ying et al. | |
| 6,256,767 B1 | 7/2001 | Kuekes et al. | |
| 6,270,074 B1 | 8/2001 | Rasmussen et al. | |
| 6,278,231 B1 | 8/2001 | Iwasaki et al. | |
| 6,286,226 B1 | 9/2001 | Jin | |
| 6,287,765 B1 | 9/2001 | Cubicciotti | |
| 6,314,019 B1 | 11/2001 | Kuekes et al. | |
| 6,325,904 B1 * | 12/2001 | Peeters | 257/414 |
| 6,340,822 B1 | 1/2002 | Brown et al. | |
| 6,346,189 B1 | 2/2002 | Dai et al. | |
| 6,355,198 B1 | 2/2002 | Kim et al. | |
| 6,359,288 B1 | 3/2002 | Ying et al. | |
| 6,437,329 B1 | 8/2002 | Yedur et al. | |
| 6,459,095 B1 | 10/2002 | Heath et al. | |
| 6,465,132 B1 | 10/2002 | Jin | |
| 6,468,657 B1 * | 10/2002 | Hou et al. | 428/403 |
| 6,468,677 B1 | 10/2002 | Benton et al. | |
| 6,503,375 B1 | 1/2003 | Mayden et al. | |
| 6,528,020 B1 * | 3/2003 | Dai et al. | 422/98 |
| 6,538,367 B1 | 3/2003 | Choi et al. | |
| 6,559,468 B1 | 5/2003 | Kuekes et al. | |
| 6,586,095 B2 | 7/2003 | Wang et al. | |
| 6,628,053 B1 | 9/2003 | Den et al. | |
| 6,741,019 B1 | 2/2004 | Filas et al. | |
| 6,716,409 B2 | 4/2004 | Hafner et al. | |
| 6,743,408 B2 * | 6/2004 | Lieber et al. | 423/447.1 |
| 6,756,025 B2 | 6/2004 | Colbert et al. | |
| 6,756,795 B2 | 6/2004 | Hunt et al. | |
| 6,762,056 B1 | 7/2004 | Peeters | |
| 6,781,166 B2 | 8/2004 | Lieber et al. | |
| 6,803,840 B2 | 10/2004 | Hunt et al. | |
| 6,808,746 B1 | 10/2004 | Dai et al. | |
| 6,815,706 B2 * | 11/2004 | Li et al. | 257/14 |
| 6,846,565 B2 | 1/2005 | Korgel et al. | |
| 6,872,645 B2 | 3/2005 | Duan et al. | |
| 6,882,051 B2 | 4/2005 | Majumdar | |
| 6,882,767 B2 | 4/2005 | Yang et al. | |
| 6,902,720 B2 | 6/2005 | McGimpsey | |
| 6,946,197 B2 | 9/2005 | Yadav et al. | |
| 6,958,216 B2 | 10/2005 | Kekkey et al. | |
| 6,962,823 B2 | 11/2005 | Empedocles et al. | |
| 6,974,706 B1 | 12/2005 | Melker et al. | |
| 6,996,147 B2 * | 2/2006 | Majumdar et al. | 372/43.01 |
| 7,048,903 B2 * | 5/2006 | Colbert et al. | 423/447.1 |
| 7,129,554 B2 * | 10/2006 | Lieber et al. | 257/414 |
| 7,172,953 B2 | 2/2007 | Lieber et al. | |
| 7,211,464 B2 | 5/2007 | Lieber et al. | |
| 7,254,151 B2 | 8/2007 | Lieber | |
| 7,256,466 B2 | 8/2007 | Lieber | |
| 7,301,199 B2 | 11/2007 | Lieber | |
| 7,303,875 B1 | 12/2007 | Bock et al. | |
| 7,385,267 B2 * | 6/2008 | Lieber et al. | 257/414 |
| 2001/0054709 A1 | 12/2001 | Heath et al. | |
| 2002/0013031 A1 | 1/2002 | Chen et al. | |
| 2002/0040805 A1 | 4/2002 | Swager | |
| 2002/0055239 A1 | 5/2002 | Tuominen et al. | |
| 2002/0084502 A1 | 7/2002 | Jang et al. | |
| 2002/0086335 A1 | 7/2002 | Massey et al. | |
| 2002/0112814 A1 | 8/2002 | Hafner et al. | |
| 2002/0117659 A1 | 8/2002 | Lieber et al. | |
| 2002/0122766 A1 | 9/2002 | Lieber et al. | |
| 2002/0130311 A1 | 9/2002 | Lieber et al. | |
| 2002/0130353 A1 | 9/2002 | Lieber et al. | |
| 2002/0146714 A1 | 10/2002 | Lieber et al. | |
| 2002/0158342 A1 | 10/2002 | Tuominen et al. | |
| 2002/0172820 A1 | 11/2002 | Majumdar et al. | |
| 2002/0175408 A1 | 11/2002 | Majumdar et al. | |
| 2002/0179434 A1 | 12/2002 | Dai et al. | |
| 2002/0187504 A1 | 12/2002 | Reich et al. | |
| 2003/0001091 A1 | 1/2003 | Nakayama et al. | |
| 2003/0003300 A1 | 1/2003 | Korgel et al. | |
| 2003/0032892 A1 | 2/2003 | Erlach et al. | |
| 2003/0048619 A1 | 3/2003 | Kaler et al. | |
| 2003/0073071 A1 | 4/2003 | Fritz et al. | |
| 2003/0089899 A1 | 5/2003 | Lieber et al. | |
| 2003/0098488 A1 | 5/2003 | O'Keeffe et al. | |
| 2003/0113713 A1 | 6/2003 | Glezer et al. | |
| 2003/0113940 A1 | 6/2003 | Erlanger et al. | |
| 2003/0121764 A1 | 7/2003 | Yang et al. | |
| 2003/0124509 A1 | 7/2003 | Kenis et al. | |
| 2003/0124717 A1 | 7/2003 | Awano et al. | |
| 2003/0134267 A1 | 7/2003 | Kang et al. | |
| 2003/0134433 A1 | 7/2003 | Gabriel et al. | |
| 2003/0135971 A1 | 7/2003 | Liberman et al. | |
| 2003/0156992 A1 | 8/2003 | Anderson et al. | |
| 2003/0186522 A1 | 10/2003 | Duan et al. | |
| 2003/0186544 A1 | 10/2003 | Matsui et al. | |
| 2003/0189202 A1 | 10/2003 | Li et al. | |
| 2003/0197456 A1 | 10/2003 | Den et al. | |
| 2003/0200521 A1 | 10/2003 | DeHon et al. | |
| 2004/0005723 A1 | 1/2004 | Empedocles et al. | |
| 2004/0026684 A1 | 2/2004 | Empedocles | |
| 2004/0067530 A1 | 4/2004 | Gruner | |
| 2004/0075464 A1 | 4/2004 | Samuelson et al. | |
| 2004/0095658 A1 | 5/2004 | Buretea et al. | |

| | | | |
|---|---|---|---|
| 2004/0106203 A1 | 6/2004 | Stasiak et al. | |
| 2004/0112964 A1 | 6/2004 | Empedocles et al. | |
| 2004/0113138 A1 | 6/2004 | DeHon et al. | |
| 2004/0113139 A1 | 6/2004 | DeHon et al. | |
| 2004/0118448 A1 | 6/2004 | Scher | |
| 2004/0136866 A1* | 7/2004 | Pontis et al. | 422/57 |
| 2004/0146560 A1 | 7/2004 | Whiteford | |
| 2004/0157414 A1 | 8/2004 | Gole et al. | |
| 2004/0188721 A1 | 9/2004 | Lieber et al. | |
| 2004/0191517 A1 | 9/2004 | Drake | |
| 2004/0213307 A1 | 10/2004 | Lieber et al. | |
| 2005/0037374 A1 | 2/2005 | Melker et al. | |
| 2005/0064185 A1 | 3/2005 | Buretea et al. | |
| 2005/0064731 A1 | 3/2005 | Park et al. | |
| 2005/0066883 A1 | 3/2005 | Dubrow et al. | |
| 2005/0072213 A1 | 4/2005 | Besnard et al. | |
| 2005/0079533 A1 | 4/2005 | Samuelson et al. | |
| 2005/0079659 A1 | 4/2005 | Duan et al. | |
| 2005/0100960 A1 | 5/2005 | Dai et al. | |
| 2005/0101026 A1 | 5/2005 | Sailor et al. | |
| 2005/0109989 A1 | 5/2005 | Whiteford et al. | |
| 2005/0110064 A1 | 5/2005 | Duan et al. | |
| 2005/0161662 A1 | 7/2005 | Majumdar et al. | |
| 2005/0181587 A1 | 8/2005 | Duan et al. | |
| 2005/0201149 A1 | 9/2005 | Duan et al. | |
| 2005/0202615 A1 | 9/2005 | Duan et al. | |
| 2005/0212079 A1 | 9/2005 | Stumbo et al. | |
| 2005/0214967 A1 | 9/2005 | Scher et al. | |
| 2005/0219788 A1 | 10/2005 | Chow et al. | |
| 2005/0230356 A1 | 10/2005 | Empedocles et al. | |
| 2005/0253137 A1 | 11/2005 | Whang et al. | |
| 2005/0287717 A1 | 12/2005 | Heald et al. | |
| 2006/0008942 A1 | 1/2006 | Romano et al. | |
| 2006/0009003 A1 | 1/2006 | Romano et al. | |
| 2006/0019472 A1 | 1/2006 | Pan et al. | |
| 2006/0054936 A1 | 3/2006 | Lieber et al. | |
| 2006/0057360 A1 | 3/2006 | Samuelson et al. | |
| 2006/0160246 A1 | 7/2006 | Massey et al. | |
| 2006/0175601 A1 | 8/2006 | Lieber et al. | |
| 2006/0237749 A1 | 10/2006 | Lieber et al. | |
| 2007/0026645 A1 | 2/2007 | Lieber et al. | |
| 2007/0032023 A1 | 2/2007 | Lieber et al. | |
| 2007/0032051 A1 | 2/2007 | Lieber et al. | |
| 2007/0032052 A1 | 2/2007 | Lieber et al. | |
| 2007/0048492 A1 | 3/2007 | Lieber et al. | |
| 2007/0158766 A1 | 7/2007 | Lieber et al. | |

FOREIGN PATENT DOCUMENTS

| | | |
|---|---|---|
| EP | 1 087 413 A2 | 3/2001 |
| EP | 1170799 A2 | 1/2002 |
| JP | 09-191104 | 7/1997 |
| JP | 11-11917 A2 | 1/1999 |
| JP | 2000-31462 | 1/2000 |
| JP | 2001/281965 A | 10/2001 |
| WO | WO 91/06036 A1 | 5/1991 |
| WO | WO 95/02709 A2 | 1/1995 |
| WO | WO 96/29629 A2 | 9/1996 |
| WO | WO 97/32571 | 9/1997 |
| WO | WO 97/33737 A1 | 9/1997 |
| WO | WO 97/34025 A1 | 9/1997 |
| WO | WO 97/34140 A1 | 9/1997 |
| WO | WO 98/39250 A1 | 9/1998 |
| WO | WO 98/48456 A1 | 10/1998 |
| WO | WO 99/24823 A1 | 5/1999 |
| WO | WO 98/42620 A1 | 10/1999 |
| WO | WO 99/63347 | 12/1999 |
| WO | WO 00/09443 A1 | 2/2000 |
| WO | WO 00/17101 A1 | 3/2000 |
| WO | WO 00/19494 A1 | 4/2000 |
| WO | WO 00/51186 A1 | 8/2000 |
| WO | WO 01/03208 A1 | 1/2001 |
| WO | WO 01/44796 | 6/2001 |
| WO | WO 02/17362 A2 | 2/2002 |
| WO | WO 02/31183 A1 | 4/2002 |
| WO | WO 02/48701 A2 | 6/2002 |
| WO | WO 02/080280 A1 | 10/2002 |
| WO | WO 02/086480 A1 | 10/2002 |
| WO | WO 03/005450 A2 | 1/2003 |
| WO | WO 03/016901 A1 | 2/2003 |
| WO | WO 03/053851 A2 | 7/2003 |
| WO | WO 03/054931 A1 | 7/2003 |
| WO | WO 03/063208 A2 | 7/2003 |
| WO | WO 2004/003535 A1 | 1/2004 |
| WO | WO 2004/010552 A1 | 1/2004 |
| WO | WO 2004/032190 A2 | 4/2004 |
| WO | WO 2004/032193 A2 | 4/2004 |
| WO | WO 2004/034025 A2 | 4/2004 |
| WO | WO 2004/038767 | 5/2004 |
| WO | WO 2005/089165 A2 | 9/2005 |
| WO | WO 2005/093831 A1 | 10/2005 |
| WO | WO 2005/094440 A2 | 10/2005 |
| WO | WO 2005/114282 A2 | 12/2005 |
| WO | WO 2006/107312 | 10/2006 |
| WO | WO 2006/132659 | 12/2006 |
| WO | WO 2007/044034 | 4/2007 |

OTHER PUBLICATIONS

Balavoine, F. "Helical Crystallization of Proteins on Carbon Nanotubes: A First Step towards the Development of New Biosensors," *Angew.Chem. Int. Ed*. 1999, 38, No. 13/14, 1912-1915.

Chen et al, "Large On-Off Ratios and Negative Differential Resistance in a Molecular Electronic Device", *Science*, Nov. 19, 1999, vol. 286, , pp. 1550-1551.

Chen, R.J. et al., "Noncovalent functionalization of carbon nanotubes for highly specific electronic biosensors," *PNAS* , Apr. 2003, 100(9):4984-4989.

Cheung, C.L., et al. "Diameter-Controlled Synthesis of Carbon Nanotubes," *J. Phys. Chem. B.*, 106, (2002), pp. 2429-2433.

Choi, K.J. et al., "Enhancement of Ferroelectricity in Strained $BaTiO_3$ Thin Films," *Science*, Nov. 2004, 306:1005-1009.

Chung et al., *Applied Physics Letters*, V76, N15, 2000, pp. 2069-2070.

Collier et al., "Electronically Configurable Molecular-Based Logic Gates", *Science*, Jul. 16, 1999, vol. 285, pp. 391-394.

Cui et al, "Diameter-controlled synthesis of single-crystal silicon nanowires", *Applied Physics Letters*, Apr. 9, 2001, vol. 78, No. 15, , pp. 2214-2216.

Cui et al. "Doping and Electrical Transport in Silicon Nanowires", *The Journal of Physical Chemistry*, Jun. 8, 2000, vol. 104, No. 22, , pp. 5213-5216.

Cui et al., "Functional Nanoscale Electronic Devices Assembled Using Silicon Nanowire Building Blocks", *Science*, Feb. 2, 2001, vol. 291, pp. 851-853.

Cui et al., "Functional nanoscale electronic devices assembled using silicon nanowire building blocks", *Science*, Feb. 2, 2001, vol. 291, pp. 851-853.

Cui et al., "Nanowire nanosensors for highly sensitive and selective detection of biological and chemical species", *Science*, Aug. 17, 2001, vol. 293, pp. 1289-1292.

Duan et al., "General Synthesis of Compound Semiconductor Nanowires", *Adv. Materials. 2000*, vol. 12, No. 4, pp. 298-302, published on Web Feb. 17, 2000.

Duan et al., "Indium phosphide nanowires as building blocks for nanoscale electronic and optoelectronic devices", Jan. 4, 2001, *Nature*, vol. 409, pp. 66-69.

Duan et al., "Laser-Assisted Catalytic Growth of Single Crystal GaN Nanowires",*J. Am. Chem. Soc. 2000*, Oct. 18, 1999, vol. 122, , pp. 188-189; published on Web Dec. 18, 1999.

Duan et al., "Nanoscale electronic and optoelectronic devices assembled from indium phosphide nanowire building blocks", supplementary article, *Nature*, 2001, vol. 409, pp. 66-69.

Duan, X. et al., "Synthesis and optical properties of gallium arsenide nanowires," *Applied Physics Letters*, Feb. 2000, 76(9):1116-1118.

Duan, X., et al., "High-performance thin-film transistors using semiconductor nanowires and nanoribbons", 2003, *Nature*, vol. 425, pp. 274-278.

Duan, X., et al., "Nonvolatile Memory and Programmable Logic from Molecule-Gated Nanowires,", *Nano Letters*, 2(5), (2002), pp. 487-490.

Duan, X., et al., "Single-nanowire electrically driven lasers," *Nature*, 421, (2003), pp. 241-245.

Esfarjani et al., Applied Physics Letters, V74, 1999, p. 79-81.

Fagan, S. "*Ab initio* calculations for a hypothetical material: Silicon nanotubes," *American Physical Society* 2000, 61, No. 15, 9994-9996.

Friedman, R.S. et al., "High-speed integrated nanowire circuits," *Nature*, Apr. 2005, 434:1085.

Givargizov, "Fundamental aspects of VSL growth", *Journal of Crystal Growth*, 1975, vol. 31, pp. 20-30.

Gradecak, S. et al., "GaN nanowire lasers with now lasing thresholds," *Applied Physics Letters*, 2005, 87:173111-1-173111-3.

Gudiksen et al. "Diameter-Selective Synthesis of Semiconductor Nanowires", *J. Am. Chem. Soc. 2000*, Jun. 6, 2000, vol. 122, pp. 8801-8802.

Gudiksen et al., "Growth of nanowire superlattice structures for nanoscale photonics and electronics", *Nature*, 2002, vol. 415, pp. 617-620.

Gudiksen, M, et al., "Size-Dependent Photoluminescence from Single Indium Phosphide Nanowires," *J. Phys. Chem. B*, 106, (2002), pp. 4036-4039.

Gudiksen, M., et al., "Synthetic Control of the Diameter and Length of Single Crystal Semiconductor Nanowires," *J. Phys. Chem. B*, 105, (2001), pp. 4062-4064.

Guo, L., et al., "A Silicon Single-Electron Transistor Memor Operating at Room Temperature," Science, vol. 275, p. 649-651, Jan. 31, 1997.

Guo, L., et al., "Nanoscale Silicon Field Effect Transistors Fabricated Using Imprint Lithography," Appl. Phys. Lett. 71 (13) Sep. 29, 1997.

Hahm, J. et al., "Direct Ultrasensitive Electrical Detection of DNA and DNA Sequence Variations Using Nanowire Nanosensors," *Nano Letters*, 2004, 4(1):51-54.

Haraguchi et al, "Polarization dependence of light emitted from GaAs p-n junctions in quantum wire crystals", *Journal of Applied Physics*, Apr. 1994, vol. 75, No. 8, pp. 4220-4225.

Haraguchi et al., "Polarization dependence of light emitted from GaAs p-n junctions in quantum wire crystals," *J.Appl.Phys.*, 1994, 75(8):4220-4225.

Haraguchi et al., Applied Physics Letters, V60, 1992, p. 745-747.

Heath, J.R. et al., "A liquid solution synthesis of single crystal germanium quantum wires," *Chemical Physics Letters*, Jun. 1993, 208(3,4):263-268.

Hiruma et al., "Self-organized growth of GaAs/InAs heterostructure nanocylinders by organometallic vapor phase epitaxy", *Journal of Crystal Growth*, 1996, vol. 163, pp. 226-231.

Hiruma, "GaAs free-standing quantum-size wires," *J Apl Phys*, 74(5): 3162-3171 (1993).

Holmes, J. et al., "Control of Thickness and Orientation of Solution-Grown Silicon Nanowires," *Science*, 287, (2000), pp. 1471-1473.

Hsu, S.T., et al. "MFMox Ferroelectric Memory Transistor," Non-Volatile Memory Technology Symposium, Orlando, FL, Nov. 15-17, 2004, p. 24-27.

Hu, J., et al., "Controlled growth and electrical properties of heterojunctions of carbon nanotubes and silicon nanowires," *Nature*, 399, (1999), pp. 48-51.

Hu, S., et al., "Serpentine Superlattice Nanowire-Array Lasers," *J of Quant. Electron.*, 8, (1995), pp. 1380-1388.

Hu, S.Y. et al., "Serpentine Superlattice Nanowire-Array Lasers," *IEEE Journal of Quantum Electronics*, Aug. 1995, 31(8):1380-1388.

Hu,J., et al., "Chemistry and Physics in One Dimension: Synthesis and Properties of Nanowires and Nanotubes," *Acc. Chem. Res.*, 32, (1999), pp. 435-445.

Huang et al., "Logic gates and computation from assembled nanowire building blocks", *Science*, 2000, vol. 287, pp. 624-625.

Huang et al., "Directed Assembly of One-dimensional Nanostructures into Functional Networks", *Science*, Jan. 26, 2001, vol. 291, pp. 630-633.

Huang et al., "Logic Gates and Computation from Assembled Nanowire Building Blocks," *Science*, 2001, 294:1313-1317.

Huang, M., et al., "Room-Temperature Ultraviolet Nanowire Nanolasers," *Science*, 292, (2001), pp. 1897-1899.

Huang, Y. et al., "Gallium Nitride Nanowire Nanodevices," Nano Letters, 2(2), (2002), pp. 101-104.

"IBM creates highest performing nanotube transistors", IBM News, 2002.

Javey, A., et al., "Ballistic Carbon nanotube field-effect transistors," *Nature*, vol. 424, pp. 654-657 (2003).

Jin et al., "Scalable Interconnection and Integration of Nanowire Devices without Registration," *NanoLetters*, 2004, 4(5):915-919.

Johnson, J., et al., "Single nanowire lasers," *J. of Phys. Chem.*, 105(46), (2001), pp. 11387-11390.

Johnson, J., et al., "Single gallium nitride nanowire lasers," *Nature*, 1, (2002), pp. 106-110.

Joselevich, E., et al., "Vectorial Growth of Metallic and Semiconducting Single-Wall Carbon Nanotubes," *Nano Letters*, 2(20), (2002), pp. 1137-1141.

Kanjanachuchai et al., "Coulomb blockade in strained-Si nanowires on leaky virtual substrates", *Semiconductor Science and Technology*, 2001, vol. 16, pp. 72-76.

Kong et al. "Nanotube molecular wires as chemical sensors", *Science*, Jan. 28, 2000, vol. 287, pp. 622-625.

Kong, J., et al., "Chemical vapor deposition of methane for single-walled carbon nanotubes," *Chem. Phys. Letters*, 292, (1998), pp. 567-574.

Kong, J., et al., "Synthesis of individual single-walled carbon nanotubes on patterned silicon wafers," *Nature*, 395, (1998), pp. 878-881.

Lauhon, L., "Epitaxial core-shell and core-multishell nanowire heterostructures,"*Nature*, 420, (2002), pp. 57-61.

Lauhon, L.J., et al., "Semiconductor Nanowire Heterostructures," Phil. Trans. R. Soc. Lond. A (2004) 362, 1247-1260.

Law, M. et al., "Nanoribbon Waveguides for Subwavelength Photonics Integration," *Science*, Aug. 2004, 305:1269-1273.

Leff, D.V. et al., "Thermodynamic Control of Gold Nanocrystal Size: Experiment and Theory," *J. Phys. Chem.*, 1995, 99:7036-7041.

Lei, B. et al., "Nanowire transistors with ferroelectric gate dielectrics: Enhanced performance and memory effects," *Applied Physics Letters*, May 2004, 84(22):4553-4555.

Lieber, "Nanoscale Science and Technology: Building a Big Future from Small Things," *MRS Bulletin*, 2003, 486-491.

Lieber, C., "Nanowire Superlattices," *Nano Letters*, Feb. 2002, 2(2):81-82.

Lu et al., "One-dimensional hole gas in germanium/silicon nanowire heterostructures," *PNAS*, 2005, 102(29):10046-10051.

Martel, R. et al., "Single-and multi-wall carbon nanotube field-effect transistors," *Applied Physics Letters*, 73(17), (1998), pp. 2447-2449.

Mcalpine, M. "High-Performance Nanowire Electronics and Photonics on Glass and Plastic Substrates", Nano Letters, 2003, pp. 1531-1535.

Mcalpine, M., "Nanoimprint ithography for Hybrid Plastic Electronics", Nano-Letters, 2003, vol. 3, No. 4, pp. 443-445.

Mcalpine, M.C. et al., "High-Performance Nanowire Electronics and Photonics and Nanoscale Patterning on Flexible Plastic Substrates," *Proceedings of the IEEE*, Jul. 2005, 93(7):1357-1363.

Menon, V.P. et al., "Fabrication and Evaluation of Nanoelectrode Ensembles," *Anal. Chem.*, Jul. 1995, 67(13):1920-1928.

Mizutani, T., et al., "Fabrication and characterization of carbon nanotube FETs," *Proceedings of SPIE*, vol. 5732, pp. 28-36 (2005).

Morales et al., *Science*, V279, 1998, pp. 208-211.

Musin, R.N., et al., "Structural and electronic properties of epitaxial core-shell nanowire heterostructures, "*Physical Review*, vol. 71, pp. 155318-1-155318-4 (2005).

Nosho, Y., et al., "n-type carbon nanotube field-effect transistors fabricated by using Ca contact electrodes," *Applied Physics Letters*, vol. 86, pp. 073105-1-073105-3 (2005).

Padeste, et al., "Modular amperometric immunosensor devices", 1995, *8th International Conference on Solid-State Sensors an Actuators and Eurosensors IX*, 357(C7): 487-490 (1995).

Patolsky, F. et al., "Electrical detection of single viruses," *PNAS*, Sep. 2004, 101(39):14017-14022.

Patolsky, F. et al., "Nanowire nanosensors," *Materials Today*, Apr. 2005, 8:20-28.

Pavesi, L., et al., "Optical gain in silicon nanocrystals," *Nature*, vol. 408, pp. 440-444 (2000).

Qi, P. et al., "Toward Large Arrays of Multiplex Functionalized Carbon Nanotube Sensors for Highly Sensitive and Selective Molecular Detection," *Nano Letters*, 2003, 3(3):347-351.

Rueckes, T., "Carbon Nanotube-Based Nonvolatile Random Access Memory for Molecular Computing," *Science*, 289, (2000), pp. 94-97.

Star, A., et al., "Preparation and Properties of Polymer-Wrapped Single-Walled Carbon Nanotubes," *Angew. Chem. Int Ed.*, 40(9), (2001), pp. 1721-1725.

Takayama, S., et al., "Patterning cells and their environments using multiple laminar fluid flows in capillary networks", Proc. Natl. Acad. Sci., 1999, Vo. 96, pp. 5545-5548.

Tang, Y.H, "Si nanowires synthesized by laser ablation of mixed SiC and $SiO_2$ powders," *Chemical Physics Letters* 1999, 314, 16-20.

Tans et al., *Nature*, V393, 1998, pp. 49-52.

Thess, A., "Cyrstalline Ropes of Metallic Carbon Nanotubes," *Science*, 273, (1996), pp. 483-487.

Tiefenauer, et al., "Towards Amperometric Immunosensor Devices" *Biosensors and Bioelectronics*, 12(3): 213-223 (1997).

Tone, L. et al., "Subwavelength-diameter silica wires for low-loss optical wave guiding," *Nature*, Dec. 2003, 426:816-819.

Urban, J. et al., "Single-Crystalline Barium Titanate Nanowires," *Adv. Mater.*, 2003, 15(5):423-426.

Vossmeyer, T. et al., "Combinatorial approaches toward patterning nanocrystals," *Journal of Applied Physics*, 1998, 84(7):3664-3670.

Wang et al., "Highly polarized photoluminescence and photodetection from single indium phosphide nanowires", *Science*, 2001, vol. 293, pp. 1455-1457.

Wang, N. et al., "$SiO_2$-enhanced synthesis of Si nanowires by laser ablation," *Applied Physics Letters*, 73(26), (1998), pp. 3902-3904.

Wang, W.U., "Label-free detection of small-molecule-protein interactions by using nanowire nanosensors," *PNAS*, 2005, 102(9):3208-3212.

Wei, Q., et al., "Synthesis of Single Crystal Bismuth-Telluride and Lead Telluride Nanowires for New Thermoelectric Materials," *Mat. Res. Soc. Symp. Proc.*, 581, (2000), pp. 219-223.

Whang, D. et al., "Nanolithography Using Hierarchically Assembled Nanowire Masks," *Nano Letters*, 2003, 3(7):951-954.

Whang, D. et al., "Large-Scale Hierarchical Organization of Nanowire Arrays for Integrated Nanosystems," *Nano Letters*, 2003, 3(9)1255-1259.

Wolf et al., "Silicon Processing for the VLSI Era", Lattice Press, V1, 2000, pp. 12-13.

Wong, S., et al., "Covalently functionalized nanotubes as nanometre-sized probes in chemistry and biology," *Nature*, 394, (1998), pp. 52-55.

Wong, S.S., et al., "Covalently functionalized nanotubes as nanometer probes for chemistry and biology," *Nature* 394, (1998), pp. 52-55.

Wu et al., "Block-by-block growth of single-crystalline Si/SiGe superlattice nanowires", web release date, Jan. 19, 2002, http://pubs.acs.org/hotartcl/nalefd/2002/n10156888_rev.html.

Wu, Y. et al., "Controlled Growth and Structures of Molecular-Scale Silicon Nanowires," *Nano Letters*, 2004, 4(3):433-436.

Wu, Y. et al., "Single-Crystal metallic nanowires and metal/semiconductor nanowire heterostructures," *Nature*, 2004, 430:61-65.

Xiang, "Ge/Si nanowire heterostructures as high-performance field-effect transistors," *Nature*, 441:489-493 (2006).

Yamada, Applied Physics Letters, V76, 2000, p. 628-630.

Yang, P., "Wires on water," *Nature*, 2003, 425:243-244.

Yang, P., et al., "Controlled Growith of ZnO Nanowires and Their Optical Properties," *Adv. Funct. Mater*, 12(5), (2002), pp. 323-331.

Yu et al, Applied Physics Letters, V72, 1998, p. 3458-3460.

Yun, W.S., et al., "Ferroelectric Properties of Individual Barium Titanate Nanowires Investigated by Scanned Probe microscopy," Nano Letters, vol. 2, No. 5, p. 447-450 (2002).

Zheng, G. et al., "Multiplexed electrical detection of cancer markers with nanowire sensor arrays," *Nature Biotechnology*, 2005, 23(10):1294-1301.

Zheng, G. et al., "Synthesis and Fabrication of High-Performance n-Type Silicon Nanowire Transistors," *Advanced Materials*, 2004, 16(21):1890-1893.

Zhong et al., "Nanowire Crossbar Arrays as Address Decoders for Integrated Nanosystems," *Science*, 2003, 302:1377-1379.

Zhong, Z. et al., "Synthesis of p-Type Gallium Nitride Nanowires for Electronic and Photonic Nanodevices," *Nano Letters*, 2003, 3(3):343-346.

Zhong, Z. et al., "Coherent Single Charge Transport in Molecular-Scale Silicon Nanowires," *Nano Letters*, 2005, 5(6):1143-1146.

Zhou, G. et al., "Growth morphology and micro-structural aspects of Si nanowires synthesized by laser ablation," J. of Crystal Growth, 197, (1999), pp. 129-135.

Notice of Allowance mailed Apr. 19, 2007 in U.S. Appl. No. 11/012,549.

Claims as allowed in U.S. Appl. No. 11/012,549.

International Preliminary Report in PCT/US2005/020974 dated Dec. 20, 2006.

International Search Report in PCT/US2005/020974 dated Dec. 20, 2006.

International Search Report in PCT/US2005/034345 dated Nov. 30, 2006.

Invitation to Pay Addition Fees from Int. Apl. No. PCT/US2005/044212, filed Dec. 6, 2005.

Office Action mailed Jan. 15, 2003 in U.S. Appl. No. 10/020,004, filed Dec. 11, 2001.

Office Action mailed Mar. 14, 2005 in U.S. Appl. No. 10/020,004, filed Dec. 11, 2001.

Office Action mailed Jun. 25, 2004 in U.S. Appl. No. 10/020,004, filed Dec. 11, 2001.

Office Action mailed Aug. 30, 2005 in U.S. Appl. No. 10/020,004, filed Dec. 11, 2001.

Office Action mailed Oct. 27, 2006 in U.S. Appl. No. 10/734,086.

Office Action mailed Nov. 2, 2006 in U.S. Appl. No. 10/196,337, filed Jul. 16, 2002.

Office Action mailed Dec. 20, 2006 in U.S. Appl. No. 11/012,549, filed Dec. 15, 2004.

Office Action mailed May 16, 2006 in U.S. Appl. No. 09/935,776, filed Aug. 22, 2001.

Search Report from International Application No. PCT/US2003/22753.

Search Report from International Application No. PCT/US2005/004459.

Search Report from International Application No. PCT/US2005/026759.

Written Opinion in PCT/US01/48230 dated Mar. 10, 2003.

Written Opinion in PCT/US2005/004459 dated Aug. 29, 2005.

Written Opinion in PCT/US2005/020974 dated Dec. 20, 2006.

Written Opinion in PCT/US2005/026759 dated Jun. 6, 2006.

Written Opinion in PCT/US2005/034345 dated Nov. 30, 2006.

Jensen, Kristine Kilsa et al. "Kinetics For Hybridization Of Peptide Nucleic Acids (PNA) with DNA and RNA Studied With The BIAcore Technique" Biochemistry 1997, 36, pp. 5072-5077.

Li, C Z et al. "Fabrication Of Stable Metallic Nanowires With Quantized Conductance" Nanotechnology 10 (1999), pp. 221-223.

Li, Z. et al. "Sequence-Specific Label-Free DNA Sensors Based on Silicon Nanowires" Nano Letters 2004, vol. 4, No. 2, pp. 245-247.

Patolsky, Fernando et al. "Nanowire Sensors For Medicine And The Life Sciences" Nanomedicine (2006) 1(1), pp. 51-65.

Soh, Hyongsok T. et al. "Integrated Nanotube Circuits: Controlled Growth And Ohmic Contracting Of Single-Walled Carbon Nanotubes" Applied Physics Letters, vol. 75, No. 5, Aug. 2, 1999, pp. 627-629.

Office Action from U.S. Appl. No. 11/082,372 dated Aug. 7, 2006.

Office Action from U.S. Appl. No. 11/543,337 dated Mar. 18, 2008.

Office Action from U.S. Appl. No. 09/935,776 dated Aug. 22, 2001.

Office Action from U.S. Appl. No. 09/935,776, dated Sep. 15, 2004.

Office Action from U.S. Appl. No. 09/935,776 dated Mar. 11, 2005.

Office Action from U.S. Appl. No. 09/935,776 dated Aug. 30, 2005.

Office Action from U.S. Appl. No. 11/012,549 dated Dec. 20, 2006.

Office Action from U.S. Appl. No. 11/582,167 dated Apr. 23, 2007.

Office Action from U.S. Appl. No. 10/196,337 dated Jun. 30, 2004.

Office Action from U.S. Appl. No. 10/196,337 dated Jan. 3, 2005.

Office Action from U.S. Appl. No. 10/196,337 dated May 25, 2005.
Office Action from U.S. Appl. No. 10/196,337 dated Feb. 23, 2006.
Office Action from U.S. Appl. No. 10/995,075 dated Nov. 29, 2005.
Office Action from U.S. Appl. No. 10/734,086 dated Apr. 7, 2006.
International Search Report and Written Opinion from PCT Application PCT/US2007/008540 dated Nov. 4, 2008.
International Search Report from PCT/US01/48230 dated Oct. 15, 2002.
International Preliminary Examination Report from PCT/US01/48230 dated May 20, 2003.
International Search Report from PCTUS2003/022061 dated Jun. 22, 2004.
International Search Report from PCT/US2002/16133 dated Nov. 27, 2003.
Office Action from U.S. Appl. No. 11/172,408 dated Dec. 29, 2008.
Office Action from U.S. Appl. No. 11/501,466 dated Feb. 5, 2009.
Office Action from U.S. Appl. No. 11/543,326 dated Mar. 5, 2009.
MacBeath, G., et al. "Printing Proteins as Microarrays for High-Throughput Function Determination," *Science*, vol. 289, pp. 1760-1762 (2000).
Mitchell, D., et al., "Smart Nanotubes for Bioseparations and Biocatalysis," *JACS*, vol. 124, pp. 11864-11865 (2002).
Neuman, H., et al., "Microarray profiling of antiviral antibodies for the development of diagnostics, vaccines, and therapeutics," *Clinical Immunology*, vol. 111, pp. 196-201 (2004).
Smalley, E., et al., "Biochip spots single viruses," *Latest Tech Research News*, pp. 1-4 (2004) website: http://www.trnmag.com/Stories/2004/102004/Biochip_spots_single_viruses_102004.html.

* cited by examiner

NANOSENSORS

RELATED APPLICATIONS

This application is a continuation of U.S. patent application Ser. No. 11/582,167, filed Oct. 17, 2006, which is a divisional of U.S. patent application Ser. No. 10/020,004, filed Dec. 11, 2001, which application claims priority under 35 U.S.C. §119(e) to commonly-owned, co-pending U.S. Provisional Patent Application Ser. Nos. 60/292,035, entitled "Nanowire and Nanotube Nanosensors," filed May 18, 2001 and 60/254,745, entitled "Nanowire and Nanotube Nanosensors," filed Dec. 11, 2000, each of which is hereby incorporated by reference in its entirety.

This invention was made with government support under DBI-98346603 awarded by the National Science Foundation, N00014-00-1-0476 awarded by the Office of Naval Research, and CA091357 awarded by the National Institutes of Health. The government has certain rights in the invention.

FIELD OF INVENTION

The present invention relates generally to nanowires and nanoscale devices and more particularly to a nanoscale device having a nanowire or functionalized nanowires for detecting the presence or absence of an analyte suspected to be present in a sample, and method for using same.

BACKGROUND OF THE INVENTION

Nanowires are ideally suited for efficient transport of charge carriers and excitons, and thus are expected to be critical building blocks for nanoscale electronics and optoelectronics. Studies of electrical transport in carbon nanotubes have led to the creation of field effect transistors, single electron transistors, and rectifying junctions.

SUMMARY OF THE INVENTION

The present invention provides a series of nanoscale devices and methods of use of the same.

In one aspect, the invention provides a nanoscale device. The device is defined by a sample exposure region and a nanowire, wherein at least a portion of the nanowire is addressable by a sample in the sample exposure region. In one embodiment, the device may further comprise a detector able to determine a property associated with the nanowire.

In another embodiment, the device is a sample cassette comprising a sample exposure region and a nanowire. At least a portion of the nanowire is addressable by a sample in the sample exposure region, and the sample cassette is operatively connectable to a detector apparatus that is able to determine a property associated with the nanowire.

In another embodiment, the device is a sensor comprising at least one nanowire and means for measuring a change in a property of the at least one nanowire.

In another embodiment, the device comprises functionalized nanowires comprising a core region of a bulk nanowire and an outer region of functional moieties.

Another aspect of the invention provides a method involving determining a property change of a nanowire when the nanowire is contacted with a sample suspected of containing an analyte.

Another method involves measuring a change in a property associated with a nanowire, when the nanowire is contacted with a sample having a volume of less than about 10 microliters.

Another method involves determining the presence or quantity of an analyte in a sample suspected of containing an analyte. A change in a property of a nanowire resulting from contacting the nanowire and the sample is measured Another method for detecting an analyte comprises contacting a nanowire with a sample and determining a property associated with the nanowire. A change in the property of the nanowire indicates the presence or quantity of the analyte in the sample.

Another method comprises contacting an electrical conductor with a sample and determining the presence or quantity of an analyte in the sample by measuring a change in a property of the conductor resultant from the contact. Less than ten molecules of the analyte contribute to the change in the property.

Another aspect of the invention provides an integrated multifunctionary system comprising a nanowire sensor, a signal interpreter, signal feedback component and an intervention delivery component.

Another aspect of the invention provides a nanowire sensor device comprising a semiconductor nanowire and a binding partner having a specificity for a selected moiety. The nanowire has an exterior surface formed thereon to form a gate electrode. The nanowire also has a first end in electrical contact with a conductor to form a source electrode and a second end in contact with a conductor to form a drain electrode.

Another aspect of the invention provides an analyte-gated field effect transistor having a predetermined current-voltage characteristic and adapted for use as a chemical or biological sensor. The field effect transistor comprises a substrate formed of a first insulating material, a source electrode, a drain electrode, and a semiconductor nanowire disposed between the source and drain electrodes, and an analyte-specific minding partner disposed on a surface of the nanowire. A binding event occurring between a target analyte and the binding partner causes a detectable change in a current-voltage characteristic of the field effect transistor. Another aspect of the invention provides an array of at least 100 analyte gate field effect transistors.

Other advantages, novel features, and objects of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 16b show another view of the nanowire of FIG. 16a.

DETAILED DESCRIPTION OF THE INVENTION

Figure 1A:
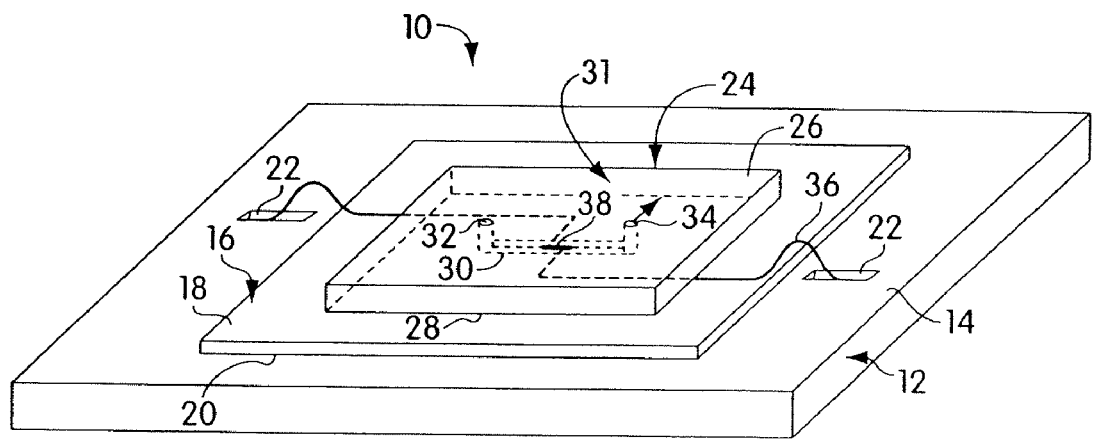
FIG. 1a illustrates, schematically, a nanoscale detector device.

The present invention provides a series of techniques and devices involving nanowires. One aspect of the invention provides functionalized nanowires. While many uses for nanowires have been developed, many more different and important uses are facilitated by the present invention where the nanowires are functionalized at their surface, or in close proximity to their surface. In one particular case, functionalization (e.g., with a reaction entity), either uniformly or non-uniformly, permits interaction of the functionalized nanowire with various entities, such as molecular entities, and the interaction induces a change in a property of the functionalized nanowire, which provides a mechanism for a nanoscale sensoring device. Another aspect of the invention is a sensor that comprises a nanowire, or a functionalized nanowire. Various aspects of the invention are described below in greater detail.

As used herein, a "nanowire" is an elongated nanoscale semiconductor which, at any point along its length, has at least one cross-sectional dimension and, in some embodiments, two orthogonal cross-sectional dimensions less than 500 nanometers, preferably less than 200 nanometers, more preferably less than 150 nanometers, still more preferably less than 100 nanometers, even more preferably less than 70, still more preferably less than 50 nanometers, even more preferably less than 20 nanometers, still more preferably less than 10 nanometers, and even less than 5 nanometers. In other embodiments, the cross-sectional dimension can be less than 2 nanometers or 1 nanometer. In one set of embodiments the nanowire has at least one cross-sectional dimension ranging from 0.5 nanometers to 200 nanometers. Where nanowires are described having a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which nanowires of the invention can be made appears below. Nanotubes are a class of nanowires that find use in the invention and, in one embodiment, devices of the invention include wires of scale commensurate with nanotubes. As used herein, a "nanotube" is a nanowire that has a hollowed-out core, and includes those nanotubes know to those of ordinary skill in the art. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used. A "wire" refers to any material having a conductivity at least that of a semiconductor or metal. For example, the term "electrically conductive" or a "conductor" or an "electrical conductor" when used with reference to a "conducting" wire or a nanowire refers to the ability of that wire to pass charge through itself. Preferred electrically conductive materials have a resistivity lower than about $10^{-3}$, more preferably lower than about $10^{-4}$, and most preferably lower than about $10^{-6}$ or $10^{-7}$ ohm-meters.

The invention provides a nanowire or nanowires preferably forming part of a system constructed and arranged to determine an analyte in a sample to which the nanowire(s) is exposed. "Determine", in this context, means to determine the quantity and/or presence of the analyte in the sample. Presence of the analyte can be determined by determining a change in a characteristic in the nanowire, typically an electrical characteristic or an optical characteristic. E.g. an analyte causes a detectable change in electrical conductivity of the nanowire or optical properties. In one embodiment, the nanowire includes, inherently, the ability to determine the analyte. The nanowire may be functionalized, i.e. comprising surface functional moieties, to which the analytes binds and induces a measurable property change to the nanowire. The binding events can be specific or non-specific. The functional moieties may include simple groups, selected from the groups including, but not limited to, —OH, —CHO, —COOH, —SO$_3$H, —CN, —NH$_2$, —SH, —COSH, COOR, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a thin coating covering the surface of the nanowire core, including, but not limited to, the following groups of materials: metals, semiconductors, and insulators, which may be a metallic element, an oxide, an sulfide, a nitride, a selenide, a polymer and a polymer gel. In another embodiment, the invention provides a nanowire and a reaction entity with which the analyte interacts, positioned in relation to the nanowire such that the analyte can be determined by determining a change in a characteristic of the nanowire.

The term "reaction entity" refers to any entity that can interact with an analyte in such a manner to cause a detectable change in a property of a nanowire. The reaction entity may enhance the interaction between the nanowire and the analyte, or generate a new chemical species that has a higher affinity to the nanowire, or to enrich the analyte around the nanowire. The reaction entity can comprise a binding partner to which the analyte binds. The reaction entity, when a binding partner, can comprise a specific binding partner of the analyte. For example, the reaction entity may be a nucleic acid, an antibody, a sugar, a carbohydrate or a protein. Alternatively, the reaction entity may be a polymer, catalyst, or a quantum dot. A reaction entity that is a catalyst can catalyze a reaction involving the analyte, resulting in a product that causes a detectable change in the nanowire, e.g. via binding to an auxiliary binding partner of the product electrically coupled to the nanowire. Another exemplary reaction entity is a reactant that reacts with the analyte, producing a product that can cause a detectable change in the nanowire. The reaction entity can comprise a coating on the nanowire, e.g. a coating of a polymer that recognizes molecules in, e.g., a gaseous sample, causing a change in conductivity of the polymer which, in turn, causes a detectable change in the nanowire.

The term "quantum dot" is known to those of ordinary skill in the art, and generally refers to semiconductor or metal nanoparticles that absorb light and quickly re-emit light in a different color depending on the size of the dot. For example, a 2 nanometer quantum dot emits green light, while a 5 nanometer quantum dot emits red light. Cadmium Selenide quantum dot nanocrystals are available from Quantum Dot Corporation of Hayward, Calif.

The term "binding partner" refers to a molecule that can undergo binding with a particular analyte, or "binding partner" thereof, and includes specific, semi-specific, and non-specific binding partners as known to those of ordinary skill in the art. E.g., Protein A is usually regarded as a "non-specific" or semi-specific binder. The term "specifically binds", when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like.

The binding may be by one or more of a variety of mechanisms including, but not limited to ionic interactions, and/or covalent interactions, and/or hydrophobic interactions, and/or van der Waals interactions, etc.

The term "fluid" is defined as a substance that tends to flow and to conform to the outline of its container: Typically fluids are materials that are unable to withstand a static shear stress. When a shear stress is applied to a fluid it experiences a continuing and permanent distortion. Typical fluids include liquids and gasses, but may also include free flowing solid particles.

The term "sample" refers to any cell, tissue, or fluid from a biological source (a "biological sample"), or any other medium, biological or non-biological, that can be evaluated in accordance with the invention including, such as serum or water. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to determine the presence or absence of a specific nucleic acid sequence.

A "sample suspected of containing" a particular component means a sample with respect to which the content of the component is unknown. For example, a fluid sample from a human suspected of having a disease, such as a neurodegenerative disease or a non-neurodegenerative disease, but not known to have the disease, defines a sample suspected of containing neurodegenerative disease. "Sample" in this context includes naturally-occurring samples, such as physiological samples from humans or other animals, samples from food, livestock feed, etc. Typical samples taken from humans or other animals include tissue biopsies, cells, whole blood, serum or other blood fractions, urine, ocular fluid, saliva, cerebro-spinal fluid, fluid or other samples from tonsils, lymph nodes, needle biopsies, etc.

The term "electrically coupled" when used with reference to a nanowire and an analyte, or other moiety such as a reaction entity, refers to an association between any of the analyte, other moiety, and the nanowire such that electrons can move from one to the other, or in which a change in an electrical characteristic of one can be determined by the other. This can include electron flow between these entities, or a change in a state of charge, oxidation, or the like that can be determined by the nanowire. As examples, electrical coupling can include direct covalent linkage between the analyte or other moiety and the nanowire, indirect covalent coupling (e.g. via a linker), direct or indirect ionic bonding between the analyte (or other moiety) and the nanowire, or other bonding (e.g. hydrophobic bonding). In some cases, no actual bonding may be required and the analyte or other moiety may simply be contacted with the nanowire surface. There also need not necessarily be any contact between the nanowire and the analyte or other moiety where the nanowire is sufficiently close to the analyte to permit electron tunneling between the analyte and the nanowire.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev. pp.* 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below (i.e. toward the Fc domain) the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the (Fab')2 dimer into an Fab' monomer. The Fab' monomer is essentially a Fab with part of the hinge region (see, Paul (1993) *Fundamental Immunology*, Raven Press, N.Y. for a more detailed description of other antibody fragments). While various antibody fragments are defined in terms of the digestion of an intact antibody, one of skill will appreciate that such fragments may be synthesized de novo either chemically, by utilizing recombinant DNA methodology, or by "phage display" methods (see, e.g., Vaughan et al. (1996) *Nature Biotechnology,* 14(3): 309-314, and PCT/US96/10287). Preferred antibodies include single chain antibodies, e.g., single chain Fv (scFv) antibodies in which a variable heavy and a variable light chain are joined together (directly or through a peptide linker) to form a continuous polypeptide.

One aspect of the invention involves a sensing element, which can be an electronic sensing element, and a nanowire able to detect the presence, or absence, of an analyte in a sample (e.g. a fluid sample) containing, or suspected of containing, the analyte. Nanoscale sensors of the invention may be used, for example, in chemical applications to detect pH or the presence of metal ions; in biological applications to detect a protein, nucleic acid (e.g. DNA, RNA, etc.), a sugar or carbohydrate, and/or metal ions; and in environmental applications to detect pH, metal ions, or other analytes of interest.

Another aspect of the present invention provides an article comprising a nanowire and a detector constructed and arranged to determine a change in an electrical property of the nanowire. At least a portion of the nanowire is addressable by a sample containing, or suspected of containing, an analyte. The phrase "addressable by a fluid" is defined as the ability of the fluid to be positioned relative to the nanowire so that an analyte suspected of being in the fluid is able to interact with the nanowire. The fluid may be proximate to or in contact with the nanowire.

In all of the illustrative embodiments described herein, any nanowire can be used, including carbon nanotubes, nanorods, nanowires, organic and inorganic conductive and semiconducting polymers, and the like unless otherwise specified. Other conductive or semiconducting elements that may not be molecular wires, but are of various small nanoscopic-scale dimension, also can be used in some instances, e.g. inorganic structures such as main group and metal atom-based wire-like silicon, transition metal-containing wires, gallium arsenide, gallium nitride, indium phosphide, germanium, cadmium selenide structures. A wide variety of these and other nanowires can be grown on and/or applied to surfaces in patterns useful for electronic devices in a manner similar to techniques described herein involving nanowires, without undue experimentation. The nanowires should be able to be formed of at least one micron, preferably at least three microns, more preferably at least five microns, and more preferably still at least ten or twenty microns in length, and preferably are less than about 100 nanometers, more preferably less than about 75 nanometers, and more preferably less than about 50 nanometers, and more preferably still less than about 25 nanometers in thickness (height and width). The wires should have an aspect ratio (length to thickness) of at least about 2:1, preferably greater than about 10:1, and more preferably greater than about 1000:1. A preferred nanowire for use in devices of the invention can be either a nanotube or a nanowire. Nanotubes (e.g. carbon nanotubes) are hollow. Nanowires (e.g. silicon nanowires) are solid.

Whether nanotubes or nanowires are selected, the criteria for selection of nanowires and other conductors or semiconductors for use in the invention are based, in some instances, mainly upon whether the nanowire itself is able to interact with an analyte, or whether the appropriate reaction entity, e.g. binding partner, can be easily attached to the surface of the nanowire, or the appropriate reaction entity, e.g. binding partner, is near the surface of the nanowire. Selection of suitable conductors or semiconductors, including nanowires, will be apparent and readily reproducible by those of ordinary skill in the art with the benefit of the present disclosure.

Nanotubes that may be used in the present invention include single-walled nanotubes (SWNTs) that exhibit unique electronic, and chemical properties that are particularly suitable for molecular electronics. Structurally, SWNTs are formed of a single graphene sheet rolled into a seamless tube with a diameter on the order of about 0.5 nm to about 5 nm and a length that can exceed about 10 microns. Depending on diameter and helicity, SWNTs can behave as one-dimensional metals or semiconductor and are currently available as a mixture of metallic and semiconducting nanotubes. Methods of manufacture of nanotubes, including SWNTs, and characterization are known. Methods of selective functionalization on the ends and/or sides of nanotubes also are known, and the present invention makes use of these capabilities for molecular electronics. The basic structural/electronic properties of nanotubes can be used to create connections or input/output signals, and nanotubes have a size consistent with molecular scale architecture.

Preferred nanowires of the present invention are individual nanowires. As used herein, "individual nanowires" means a nanowire free of contact with another nanowire (but not excluding contact of a type that may be desired between individual nanowires in a crossbar array). For example, typical individual nanowire can have a thickness as small as about 0.5 nm. This is in contrast to nanowires produced primarily by laser vaporization techniques that produce high-quality materials, but materials formed as ropes having diameters of about 2 to about 50 nanometers or more and containing many individual nanowires (see, for example, Thess, et al., "Crystalline Ropes of Metallic Carbon Nanotubes" *Science* 273, 483-486 (1996), incorporated herein by reference). While nanowire ropes can be used in the invention, individual nanowires are preferred.

The invention may utilize metal-catalyzed CVD to synthesize high quality individual nanowires such as nanotubes for molecular electronics. CVD synthetic procedures needed to prepare individual wires directly on surfaces and in bulk form are known, and can readily be carried out by those of ordinary skill in the art. See, for example, Kong, et al., "Synthesis of Individual Single-Walled Carbon Nanotubes on Patterned Silicon Wafers", *Nature* 395, 878-881 (1998); Kong, et al., "Chemical Vapor Deposition of Methane for Single-Walled Carbon Nanotubes" *Chem. Phys. Lett.* 292, 567-574 (1998), both incorporated herein by reference. Nanowires may also be grown through laser catalytic growth. See, for example, Morales et al. "A Laser Ablation Method for the Synthesis of Crystalline Semiconductor Nanowires" *Science* 279, 208-211 (1998), incorporated herein by reference.

Alternatively, the nanowire may comprise a semiconductor that is doped with an appropriate dopant to create an n-type or p-type semiconductor as desired. For example, silicon may be doped with boron, aluminum, phosphorous, or arsenic. Laser catalytic growth may be used to introduce controllably the dopants during the vapor phase growth of silicon nanowires.

Controlled doping of nanowires can be carried out to form, e.g., n-type or p-type semiconductors. In various embodiments, this invention involves controlled doping of semiconductors selected from among indium phosphide, gallium arsenide, gallium nitride, cadmium selenide, and zinc selenide. Dopants including, but not limited to, zinc, cadmium, or magnesium can be used to form p-type semiconductors in this set of embodiments, and dopants including, but not limited to, tellurium, sulfur, selenium, or germanium can be used as dopants to form n-type semiconductors from these materials. These materials define direct band gap semiconductor materials and these and doped silicon are well known to those of ordinary skill in the art. The present invention contemplates use of any doped silicon or direct band gap semiconductor materials for a variety of uses.

As examples of nanowire growth, placement, and doping, SiNWs (elongated nanoscale semiconductors) may be synthesized using laser assisted catalytic growth (LCG). As shown in FIGS. 2 and 3, laser vaporization of a composite target that is composed of a desired material (e.g. InP) and a catalytic material (e.g. Au) creates a hot, dense vapor which quickly condenses into liquid nanoclusters through collision with the buffer gas. Growth begins when the liquid nanoclusters become supersaturated with the desired phase and continues as long as the reactant is available. Growth terminates when the nanowires pass out of the hot reaction zone or when the temperature is turned down. Au is generally used as catalyst for growing a wide range of elongated nanoscale semiconductors. However, the catalyst is not limited to Au only. A wide rage of materials such as (Ag, Cu, Zn, Cd, Fe, Ni, Co . . . ) can be used as the catalyst. Generally, any metal that can form an alloy with the desired semiconductor material, but doesn't form more stable compound than with the elements of the desired semiconductor can be used as the catalyst. The buffer gas can be Ar, N2, and others inert gases. Sometimes, a mixture of H2 and buffer gas is used to avoid undesired oxidation by residue oxygen. Reactive gas can also be introduced when desired (e.g. ammonia for GaN). The key point of this process is laser ablation generates liquid nanoclusters that subsequently define the size and direct the growth direction of the crystalline nanowires. The diameters of the resulting nanowires are determined by the size of the catalyst cluster, which in turn can be varied by controlling the growth conditions (e.g. background pressure, temperature, flow rate . . . ). For example, lower pressure generally produces nanowires with smaller diameters. Further diameter control can be done by using uniform diameter catalytic clusters.

With same basic principle as LCG, if uniform diameter nanoclusters (less than 10-20% variation depending on how uniform the nanoclusters are) are used as the catalytic cluster, nanowires with uniform size (diameter) distribution can be produced, where the diameter of the nanowires is determined by the size of the catalytic clusters, as illustrated in FIG. 4. By controlling the growth time, nanowires with different lengths can be grown.

With LCG, nanowires can be flexibly doped by introducing one or more dopants into the composite target (e.g., Ge for n-type doping of InP). The doping concentration can be controlled by controlling the relative amount of doping element, typically 0-20%, introduced in the composite target.

Laser ablation may be used as the way to generate the catalytic clusters and vapor phase reactant for growth of nanowires and other related elongated nanoscale structures, but fabrication is not limited to laser ablation. Many ways can be used to generate vapor phase and catalytic clusters for nanowire growth (e.g. thermal evaporation).

Another technique that may be used to grow nanowires is catalytic chemical vapor deposition (C-CVD). C-CVD utilizes the same basic principles as LCG, except that in the C-CVD method, the reactant molecules (e.g., silane and the dopant) are from vapor phase molecules (as opposed to vapor source from laser vaporization.

In C-CVD, nanowires can be doped by introducing the doping element into the vapor phase reactant (e.g. diborane and phosphane for p-type and n-type doped nanowire). The doping concentration can be controlled by controlling the relative amount of the doping element introduced in the composite target. It is not necessary to obtain elongated nanoscale semiconductors with the same doping ratio as that in the gas reactant. However, by controlling the growth conditions (e.g. temperature, pressure . . . ), nanowires with same doping concentration can be reproduced. And the doping concentration can be varied over a large range by simply varying the ratio of gas reactant (e.g. 1 ppm-10%).

There are several other techniques that may be used to grow elongated nanoscale semiconductors such as nanowires. For example, nanowires of any of a variety of materials can be grown directly from vapor phase through a vapor-solid process. Also, nanowires can also be produced by deposition on the edge of surface steps, or other types of patterned surfaces, as shown in FIG. 5. Further, nanowires can be grown by vapor deposition in/on any general elongated template, for example, as shown in FIG. 6. The porous membrane can be porous silicon, anodic alumina or diblock copolymer and any other similar structure. The natural fiber can be DNA molecules, protein molecules carbon nanotubes, any other elongated structures. For all the above described techniques, the source materials can be came from a solution phase rather than a vapor phase. While in solution phase, the template can also be column micelles formed by surfactant molecules in addition to the templates described above.

Using one or more of the above techniques, elongated nanoscale semiconductors, including semiconductor nanowires and doped semiconductor nanowires, can be grown. Such bulk-doped semiconductors may include various combinations of materials, including semiconductors and dopants. The following are non-comprehensive lists of such materials. Other materials may be used. Such materials include, but are not limited to:

Elemental Semiconductors:
   Si, Ge, Sn, Se, Te, B, Diamond, P

Solid Solution of Elemental Semiconductors:
   B—C, B—P(BP6), B—Si, Si—C, Si—Ge, Si—Sn, Ge—Sn IV-IV Group Semiconductors:
   SiC III-V Semiconductors:
   BN/BP/BAs, AlN/AlP/AlAs/AlSb, GaN/GaP/GaAs/GaSb, InN/InP/InAs/InSb, Alloys of III-V Group:
   any combination of two or more of the above compound (e.g.: AlGaN, GaPAs, InPAs, GaInN, AlGaInN, GaIn AsP . . . )

II-VI Semiconductors:
   ZnO/ZnS/ZnSe/ZnTe, CdS/CdSe/CdTe, HgS/HgSe/HgTe, BeS/BeSe/BeTe/MgS/MgSe Alloys of II-VI Group: any combination of two or more of the above compound (e.g.: (ZnCd)Se, Zn(SSe) . . . )

Alloy of II-VI and III-V Semiconductors:
   combination of any one II-VI and one III-V compounds, e.g. $(GaAs)_x(ZnS)_{1-x}$ IV-VI Semiconductors:
   GeS, GeSe, GeTe, SnS, SnSe, SnTe, PbO, PbS, PbSe, PbTe I-VII Semiconductors:
   CuF, CuCl, CuBr, CuI, AgF, AgCl, AgBr, AgI Other Semiconductor Compounds:
   II-IV-$V_2$: BeSiN2, CaCN2, ZnGeP2, CdSnAs2, ZnSn Sb2 . . .
   I-$IV_2$-$V_3$: CuGeP3, CuSi2P3.
   I-III-$VI_2$: Cu, Ag)(Al, Ga, In, Tl, Fe)(S, Se, Te)2
   $IV_3$-$V_4$: Si3N4, Ge3N4 . . .
   $III_2$-$VI_3$: Al2O3, (Al, Ga, In)2(S, Se, Te)3 . . .
   $III_2$-IV-VI: Al2CO . . .

For Group IV semiconductor materials, a p-type dopant may be selected from Group III, and an n-type dopant may be selected from Group V. For silicon semiconductor materials, a p-type dopant may be selected from the group consisting of B, Al and In, and an n-type dopant may be selected from the group consisting of P, As and Sb. For Group III-V semiconductor materials, a p-type dopant may be selected from Group II, including Mg, Zn, Cd and Hg, or Group IV, including C and Si. An n-type dopant may be selected from the group consisting of Si, Ge, Sn, S, Se and Te. It will be understood that the invention is not limited to these dopants.

Nanowires may be either grown in place or deposited after growth. Assembly, or controlled placement of nanowires on surfaces after growth can be carried out by aligning nanowires using an electrical field. An electrical field is generated between electrodes, nanowires are positioned between the electrodes (optionally flowed into a region between the electrodes in a suspending fluid), and will align in the electrical field and thereby can be made to span the distance between and contact each of the electrodes.

In another arrangement individual contact points are arranged in opposing relation to each other, the individual contact points being tapered to form a point directed towards each other. An electric field generated between such points will attract a single nanowire spanning the distance between, and contacting each of, the electrodes. In this way individual nanowires can readily be assembled between individual pairs of electrical contacts. Crossed-wire arrangements, including multiple crossings (multiple parallel wires in a first direction crossed by multiple parallel wires in a perpendicular or approximately perpendicular second direction) can readily be formed by first positioning contact points (electrodes) at locations where opposite ends of the crossed wires desirably will lie. Electrodes, or contact points, can be fabricated via typical microfabrication techniques.

These assembly techniques can be substituted by, or complemented with, a positioning arrangement involving positioning a fluid flow directing apparatus to direct fluid containing suspended nanowires toward and in the direction of alignment with locations at which nanowires are desirably positioned.

Another arrangement involves forming surfaces including regions that selectively attract nanowires surrounded by regions that do not selectively attract them. For example, —NH$_2$ can be presented in a particular pattern at a surface, and that pattern will attract nanowires or nanotubes having surface functionality attractive to amines. Surfaces can be patterned using known techniques such as electron-beam patterning, "soft-lithography" such as that described in International Patent Publication No. WO 96/29629, published Jul. 26, 1996, or U.S. Pat. No. 5,512,131, issued Apr. 30, 1996, each of which is incorporated herein by reference.

A technique is also known to direct the assembly of a pre-formed nanowire onto a chemically patterned self-assembled monolayer. In one example of patterning the SAM for directed assembly of nanoscale circuitry atomic force microscopy (AFM) is used to write, at high resolution, a pattern in SAM at which the SAM is removed. The pattern can be for example linear for parallel arrays, or a crossed array of lines linear in embodiments for making nanoscopic crossed arrays. In another technique, microcontact printing can be used to apply patterned SAM to the substrate. Next, open areas in the patterned surface (the SAM-free linear region between linear SAM) are filled with an amino-terminated SAM that interacts in a highly specific manner with a nanowire such as a nanotube. The result is a patterned SAM, on a substrate, including linear SAM portions separated by a line of amino-terminated SAM material. Of course, any desired pattern can be formed where regions of the amino-terminated SAM material corresponds to regions at which wire deposition is desired. The patterned surface then is dipped into a suspension of wires, e.g. nanotubes, and rinsed to create an array in which wires are located at regions of the SAM. Where nanotubes are used, an organic solvent such as dimethyl formamide can be used to create the suspension of nanotubes. Suspension and deposition of other nanowires is achievable with easily selected solvents.

Any of a variety of substrates and SAM-forming materials can be used along with microcontact printing techniques, such as those described in International Patent Publication WO 96/29629 of Whitesides, et al., published Jun. 26, 1996 and incorporated herein by reference. Patterned SAM surfaces can be used to direct a variety of nanowires or nanoscale electronic elements. SAM-forming material can be selected, with suitable exposed chemical functionality, to direct assembly of a variety of electronic elements. Electronic elements, including nanotubes, can be chemically tailored to be attracted specifically to specific, predetermined areas of a patterned SAM surface. Suitable functional groups include, but are not limited to SH, NH$_3$, and the like. Nanotubes are particularly suitable for chemical functionalization on their exterior surfaces, as is well known.

Chemically patterned surfaces other than SAM-derivatized surfaces can be used, and many techniques for chemically patterning surfaces are known. Suitable exemplary chemistries and techniques for chemically patterning surfaces are described in, among other places, International Patent Publication No. WO 97/34025 of Hidber, et al, entitled, "Microcontact Printing of Catalytic Colloids", and U.S. Pat. Nos. 3,873,359; 3,873,360; and 3,900,614, each by Lando, all of these documents incorporated herein by reference. Another example of a chemically patterned surface is a micro-phase separated block copolymer structure. These structures provide a stack of dense lamellar phases. A cut through these phases reveals a series of "lanes" wherein each lane represents a single layer. The block copolymer is typically an alternating block and can provide varying domains by which to dictate growth and assembly of a nanowire. Additional techniques are described in International Patent Publication No. WO 01/03208 published Jan. 11, 2001 by Lieber, et al., incorporated herein by reference.

Chemical changes associated with the nanowires used in the invention can modulate the properties of the wires and create electronic devices of a variety of types. Presence of the analyte can change the electrical properties of the nanowire through electrocoupling with a binding agent of the nanowire. If desired, the nanowires can be coated with a specific reaction entity, binding partner or specific binding partner, chosen for its chemical or biological specificity to a particular analyte.

The reaction entity is positioned relative to the nanowire to cause a detectable change in the nanowire. The reaction entity may be positioned within 100 nanometers of the nanowire, preferably with in 50 nanometers of the nanowire, and more preferably with in 10 nanometers of the nanowire, and the proximity can be determined by those of ordinary skill in the art. In one embodiment, the reaction entity is positioned less than 5 nanometers from the nanoscopic wire. In alternative embodiments, the reaction entity is positioned with 4 nm, 3 nm, 2 nm, and 1 nm of the nanowire. In a preferred embodiment, the reaction entity is attached to the nanowire through a linker.

As used herein, "attached to," in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "attached" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is covalently attached to a bead, a binding species that forms a part (via genetic engineering) of a molecule such as GST or, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. "Covalently attached" means attached via one or more covalent bonds. E.g. a species that is covalently coupled, via EDC/NHS chemistry, to a carboxylate-presenting alkyl thiol which is in turn attached to a gold surface, is covalently attached to that surface.

Another aspect of the invention involves an article comprising a sample exposure region and a nanowire able to detect the presence of absence of an analyte. The sample exposure region may be any region in close proximity to the nanowire wherein a sample in the sample exposure region addresses at least a portion of the nanowire. Examples of sample exposure regions include, but are not limited to, a well, a channel, a microchannel, and a gel. In preferred embodiments, the sample exposure region holds a sample proximate the nanowire, or may direct a sample toward the nanowire for determination of an analyte in the sample. The nanowire may be positioned adjacent to or within the sample exposure region. Alternatively, the nanowire may be a probe that is inserted into a fluid or fluid flow path. The nanowire probe may also comprise a micro-needle and the sample exposure region may be addressable by a biological sample. In this arrangement, a device that is constructed and arranged for insertion of a micro-needle probe into a biological sample will include a region surrounding the micro-needle that defines the sample exposure region, and a sample in the sample exposure region is addressable by the nanowire, and vice-versa. Fluid flow channels can be created at a size and scale advantageous for use in the invention (microchannels) using a variety of techniques such as those described in International Patent Publication No. WO 97/33737, published Sep. 18, 1997, and incorporated herein by reference.

In another aspect of the invention, an article may comprise a plurality of nanowires able to detect the presence or absence of a plurality of one or more analytes. The individual nanowires may be differentially doped as described above, thereby varying the sensitivity of each nanowire to the analyte. Alternatively, individual nanowires may be selected based on their ability to interact with specific analytes, thereby allowing the detection of a variety of analytes. The plurality of nanowires may be randomly oriented or parallel to one another. Alternatively, the plurality of nanowires may be oriented in an array on a substrate.

FIG. 1a shows one example of an article of the present invention. In FIG. 1a, nanoscale detector device 10 is comprised of a single nanowire 38 positioned above upper surface 18 of substrate 16. Chip carrier 12 has an upper surface 14 for supporting substrate 16 and electrical connections 22. Chip carrier 12, may be made of any insulating material that allows connection of electrical connections 22 to electrodes 36. In a preferred embodiment, the chip carrier is an epoxy. Upper surface 14 of the chip carrier, may be of any shape including, for example, planar, convex, and concave. In a preferred embodiment, upper surface 14 of the chip carrier is planar.

As shown in FIG. 1a, lower surface of 20 of substrate 16 is positioned adjacent to upper surface 14 of the chip carrier and supports electrical connection 22. Substrate 16 may typically be made of a polymer, silicon, quartz, or glass, for example. In a preferred embodiment, the substrate 16 is made of silicon coated with 600 nm of silicon oxide. Upper surface 18 and lower surface 20 of substrate 16 may be of any shape, such as planar, convex, and concave. In a preferred embodiment, lower surface 20 of substrate 16 contours to upper surface 14 of chip carrier 12. Similarly, mold 24 has an upper surface 26 and a lower surface 28, either of which may be of any shape. In a preferred embodiment, lower surface 28 of mold 24 contours to upper surface 18 of substrate 16.

Figure 3A:
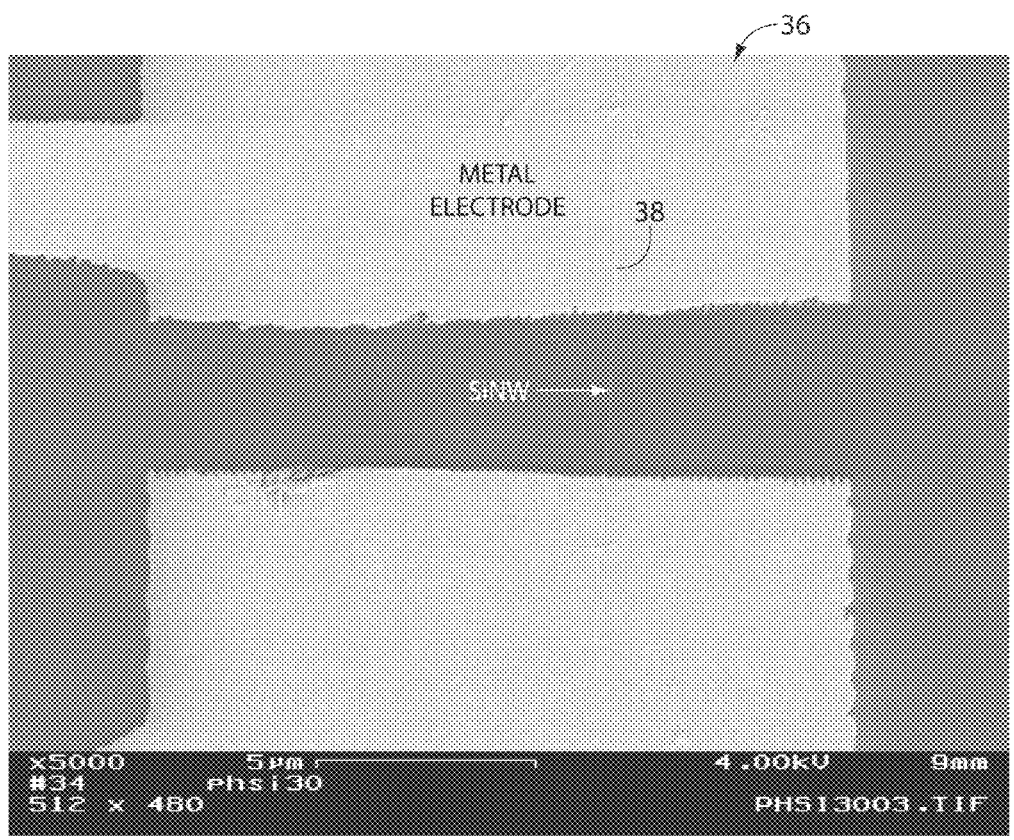
FIG. 3a is a low resolution scanning electron micrograph of a single silicon nanowire connected to two metal electrodes.
Figure 3B:
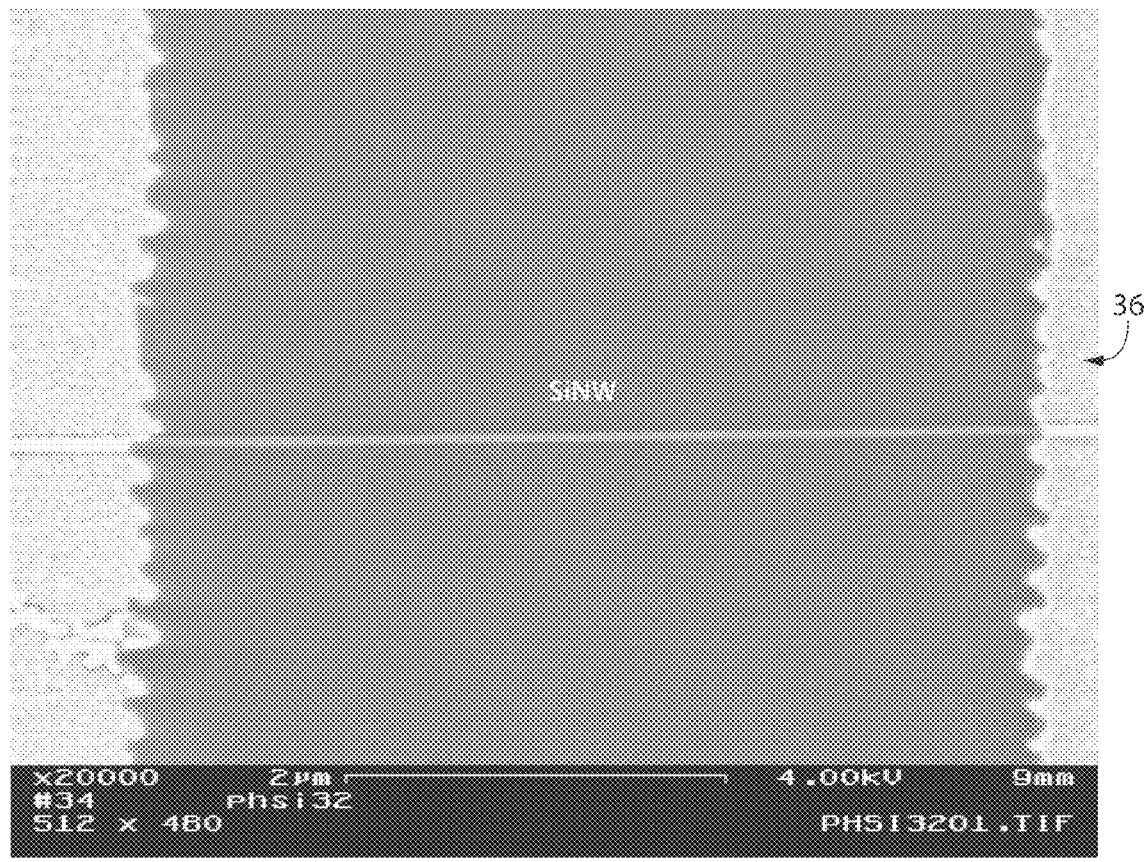
FIG. 3b is a high resolution scanning electron micrograph of a single silicon nanowire device connected to two metal electrodes.
Figure 7:
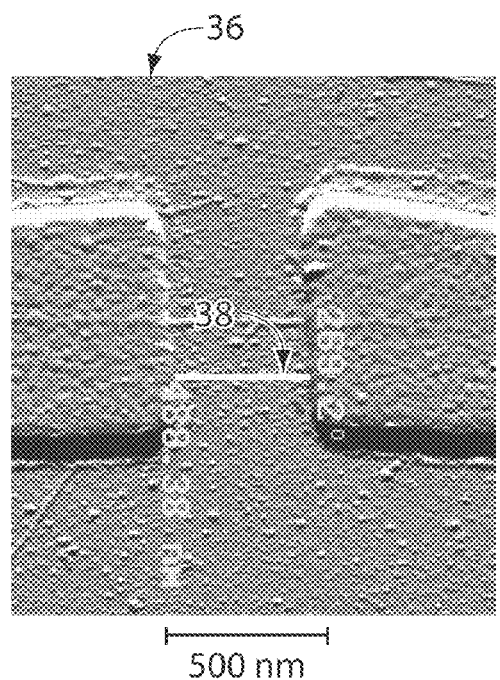
FIG. 7 is an atomic force microscopy image of a typical single wall nanotube detector device.

Mold 24 has a sample exposure region 30, shown here as a microchannel, having a fluid inlet 32 and fluid outlet 34, shown in FIG. 1a on the upper surface 26 of mold 24. Nanowire 38 is positioned such that at least a portion of the nanowire is positioned within sample exposure region 30. Electrodes 36 connect nanowire 38 to electrical connection 22. Electrical connections 22 are, optionally, connected to a detector (not shown) that measures a change in an electrical, or other property of the nanowire. FIGS. 3a and 3b are low and high resolution scanning electron micrographs, respectively, of one embodiment of the present invention. A single silicon nanowire 38 is connected to two metal electrodes 36. FIG. 7 shows an atomic force microscopy image of a typical SWNT positioned with respect to two electrodes. As seen in FIG. 7, the distance between electrodes 36 is about 500 nm. In certain preferred embodiments, electrode distances will range from 50 nm to about 20000 nm 1, more preferably from about 100 nm to about 10000 nm, and most preferably from about 500 nm to about 5000 nm.

Where a detector is present, any detector capable of determining a property associated with the nanowire can be used. The property can be electronic, optical, or the like. An electronic property of the nanowire can be, for example, its conductivity, resistivity, etc. An optical property associated with the nanowire can include its emission intensity, or emission wavelength where the nanowire is an emissive nanowire where emission occurs at a p-n junction. For example, the detector can be constructed for measuring a change in an electronic or magnetic property (e.g. voltage, current, conductivity, resistance, impedance, inductance, charge, etc.) can be used. The detector typically includes a power source and a voltmeter or amp meter. In one embodiment, a conductance less than 1 nS can be detected. In a preferred embodiment, a conductance in the range of thousandths of a nS can be detected. The concentration of a species, or analyte, may be detected from less than micromolar to molar concentrations and above. By using nanowires with known detectors, sensitivity can be extended to a single molecule. In one embodiment, an article of the invention is capable of delivering a stimulus to the nanowire and the detector is constructed and arranged to determine a signal resulting from the stimulus. For example, a nanowire including a p-n junction can be delivered a stimulus (electronic current), where the detector is constructed and arranged to determine a signal (electromagnetic radiation) resulting from the stimulus. In such an arrangement, interaction of an analyte with the nanowire, or with a reaction entity positioned proximate the nanowire, can affect the signal in a detectable manner. In another example, where the reaction entity is a quantum dot, the quantum dot may be constructed to receive electromagnetic radiation of one wavelength and emit electromagnetic radiation of a different wavelength. Where the stimulus is electromagnetic radiation, it can be affected by interaction with an analyte, and the detector can detect a change in a signal resulting therefrom. Examples of stimuli include a constant current/voltage, an alternating voltage, and electromagnetic radiation such as light.

In one example, a sample, such as a fluid suspected of containing an analyte that is to be detected and/or quantified, e.g. a specific chemical contacts nanoscopic wire 38 having a corresponding reaction entity at or near nanoscopic wire 38.

An analyte present in the fluid binds to the corresponding reaction entity and causes a change in electrical properties of the nanowire that is detected, e.g. using conventional electronics. If the analyte is not present in the fluid, the electrical properties of the nanowire will remain unchanged, and the detector will measure a zero change. Presence or absence of a specific chemical can be determined by monitoring changes, or lack thereof, in the electrical properties of the nanowire. The term "determining" refers to a quantitative or qualitative analysis of a species via, piezoelectric measurement, electrochemical measurement, electromagnetic measurement, photodetection, mechanical measurement, acoustic measurement, gravimetric measurement and the like. "Determining" also means detecting or quantifying interaction between species, e.g. detection of binding between two species.

Particularly preferred flow channels 30 for use in this invention are "microchannels". The term microchannel is used herein for a channel having dimensions that provide low Reynolds number operation, i.e., for which fluid dynamics are dominated by viscous forces rather than inertial forces. Reynolds number, sometimes referred to the ratio of inertial forces to viscous forces is given as:

$$Re = \rho d^2/\eta \tau + \rho u d/\eta$$

where u is the velocity vector, $\rho$ is the fluid density, $\eta$ is the viscosity of the fluid, d is the characteristic dimension of the channel, and $\tau$ is the time scale over which the velocity is changing (where $u/\tau = \delta u/dt$). The term "characteristic dimension" is used herein for the dimension that determines Reynolds number, as is known in the art. For a cylindrical channel it is the diameter. For a rectangular channel, it depends primarily on the smaller of the width and depth. For a V-shaped channel it depends on the width of the top of the "V", and so forth. Calculation of Re for channels of various morphologies can be found in standard texts on fluid mechanics (e.g. Granger (1995) *Fluid Mechanics*, Dover, N.Y.; Meyer (1982) *Introduction to Mathematical Fluid Dynamics*, Dover, N.Y.).

Fluid flow behavior in the steady state ($\tau \rightarrow$ infinity) is characterized by the Reynolds number, $Re = \rho u d/\eta$. Because of the small sizes and slow velocities, microfabricated fluid systems are often in the low Reynolds number regime (Re less than about 1). In this regime, inertial effects, that cause turbulence and secondary flows, and therefore mixing within the flow, are negligible and viscous effects dominate the dynamics. Under these conditions, flow through the channel is generally laminar. In particularly preferred embodiments, the channel with a typical analyte-containing fluid provides a Reynolds number less than about 0.001, more preferably less than about 0.0001.

Since the Reynolds number depends not only on channel dimension, but on fluid density, fluid viscosity, fluid velocity and the timescale on which the velocity is changing, the absolute upper limit to the channel diameter is not sharply defined. In fact, with well designed channel geometries, turbulence can be avoided for R<100 and possibly for R<1000, so that high throughput systems with relatively large channel sizes are possible. The preferred channel characteristic dimension range is less than about 1 millimeter, preferably less than about 0.5 mm, and more preferably less than about 200 microns.

In one embodiment, the sample exposure region, such as a fluid flow channel 30 may be formed by using a polydimethyl siloxane (PDMS) mold. Channels can be created and applied to a surface, and a mold can be removed. In certain embodiments, the channels are easily made by fabricating a master by using photolithography and casting PDMS on the master, as described in the above-referenced patent applications and international publications. Larger-scale assembly is possible as well.

Figure 1B:
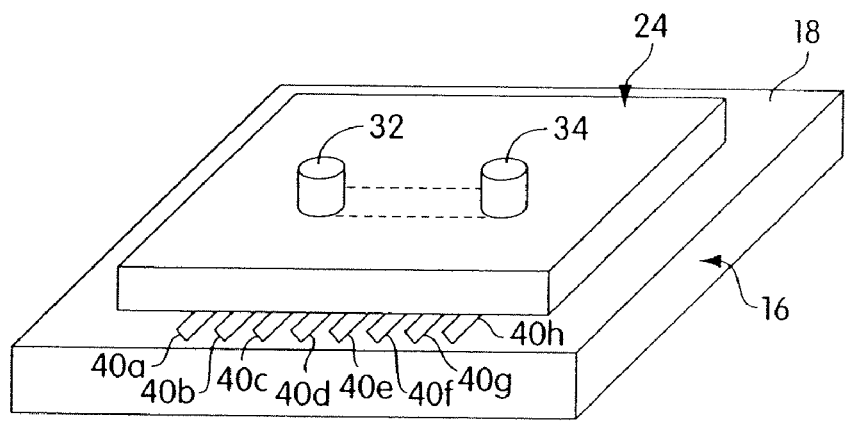
FIG. 1b illustrates, schematically, a nanoscale detector device with a parallel array of nanowires.

FIG. 1b shows an alternative embodiment of the present invention wherein the nanoscale detector device 10 of FIG. 1a further includes multiple nanowires 38a-h (not shown). In FIG. 1b, wire interconnects 40a-h connect corresponding nanowires 38a-h to electrical connections 22a-h, respectively (not shown). In a preferred embodiment, each nanowire 38a-h has a unique reaction entity selected to detect a different analytes in the fluid. In this way, the presence or absence of several analytes may be determined using one sample while performing one test.

Figure 2A:
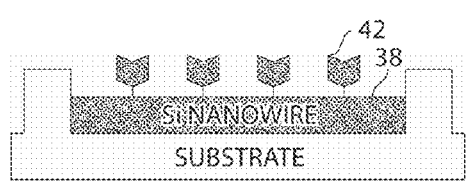
FIG. 2a illustrates, schematically, a nanoscale detector device in which a nanowire has been modified with a binding agent for detection of a complementary binding partner.
Figure 2B:
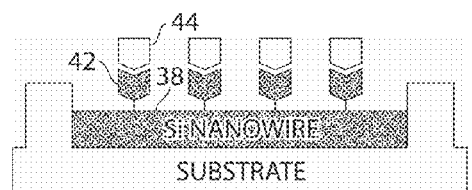
FIG. 2b illustrates, schematically, the nanoscale detector device of FIG. 2a, in which a complementary binding partner is fastened to the binding agent.

FIG. 2a schematically shows a portion of a nanoscale detector device in which the nanowire 38 has been modified with a reactive entity that is a binding partner 42 for detecting analyte 44. FIG. 2b schematically shows a portion of the nanoscale detector device of FIG. 2a, in which the analyte 44 is attached to the specific binding partner 42. Selectively functionalizing the surface of nanowires can be done, for example, by functionalizing the nanowire with a siloxane derivative. For example, a nanowire may be modified after construction of the nanoscale detector device by immersing the device in a solution containing the modifying chemicals to be coated. Alternatively, a micro-fluidic channel may be used to deliver the chemicals to the nanowires. For example, amine groups may be attached by first making the nanoscale detector device hydrophilic by oxygen plasma, or an acid and/or oxidizing agent and the immersing the nanoscale detector device in a solution containing amino silane. By way of example, DNA probes may be attached by first attaching amine groups as described above, and immersing the modified nanoscale detector device in a solution containing bifunctional crosslinkers, if necessary, and immersing the modified nanoscale detector device in a solution containing the DNA probe. The process may be accelerated and promoted by applying a bias voltage to the nanowire, the bias voltage can be either positive or negative depending on the nature of reaction species, for example, a positive bias voltage will help to bring negatively charged DNA probe species close to the nanowire surface and increase its reaction chance with the surface amino groups.

Figure 4A:
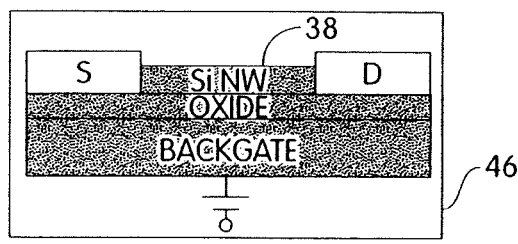
FIG. 4a shows schematically another embodiment of a nanoscale sensor having a backgate.
Figure 4B:
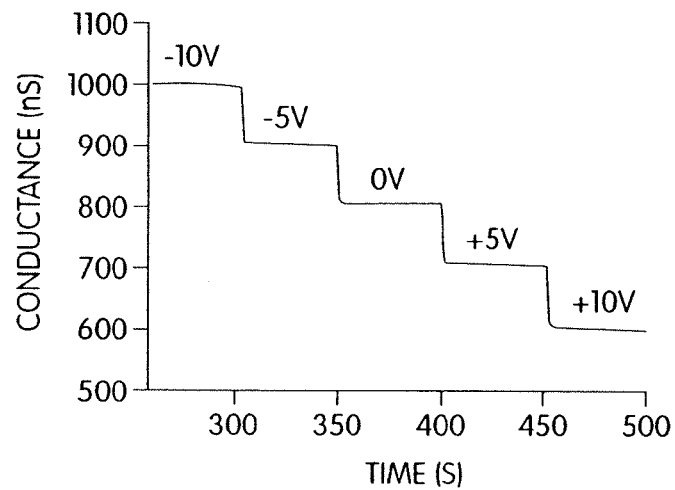
FIG. 4b shows conductance vs. time with various backgate voltages.
Figure 4C:
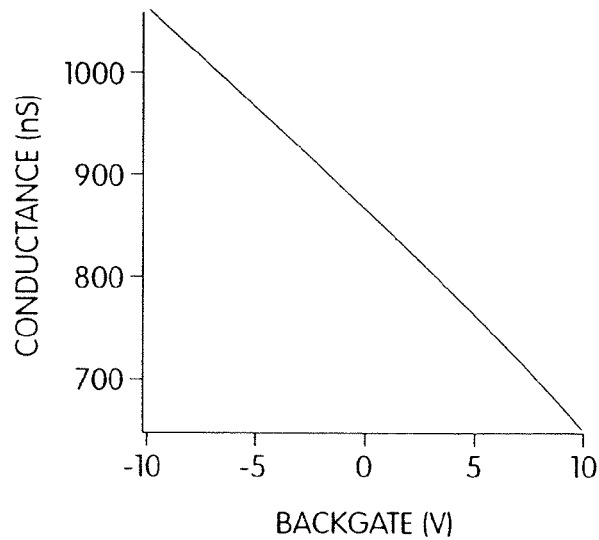
FIG. 4c shows conductance vs. backgate voltage.

FIG. 4a schematically shows another embodiment of a nanoscale sensor having a backgate 46. FIG. 4b shows conductance vs. time at with a backgate voltage ranging from −10V to +10V. FIG. 4c shows conductance vs. backgate voltage. The backgate can be used to inject or withdraw the charge carriers from the nanowire. Therefore, it may be used to control the sensitivity and the dynamic range of the nanowire sensor and to draw analytes to the nanowire.

Figure 5A:
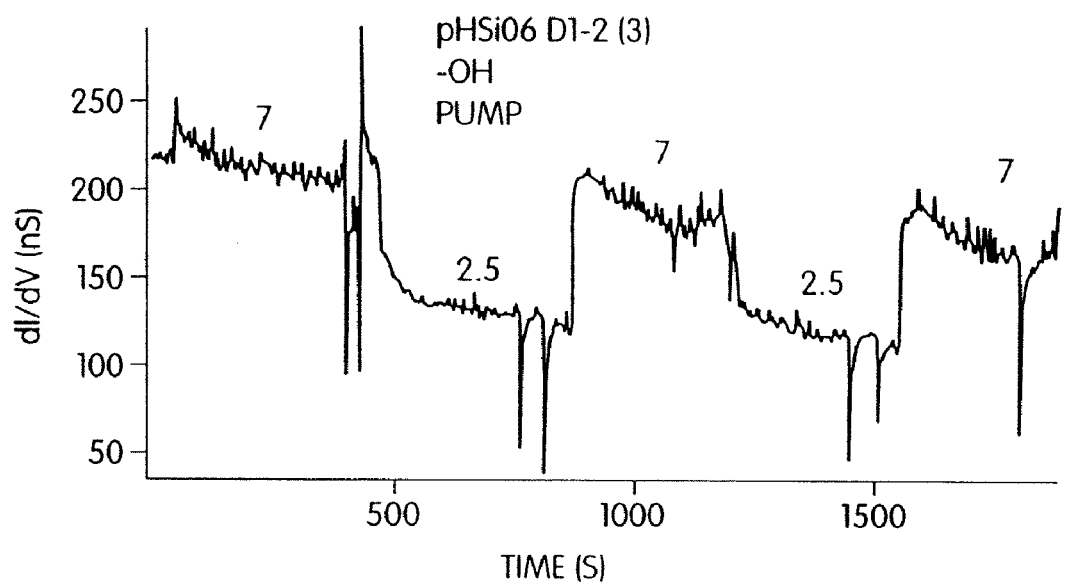
FIG. 5a shows conductance for a single silicon nanowire as a function of pH.
Figure 5B:
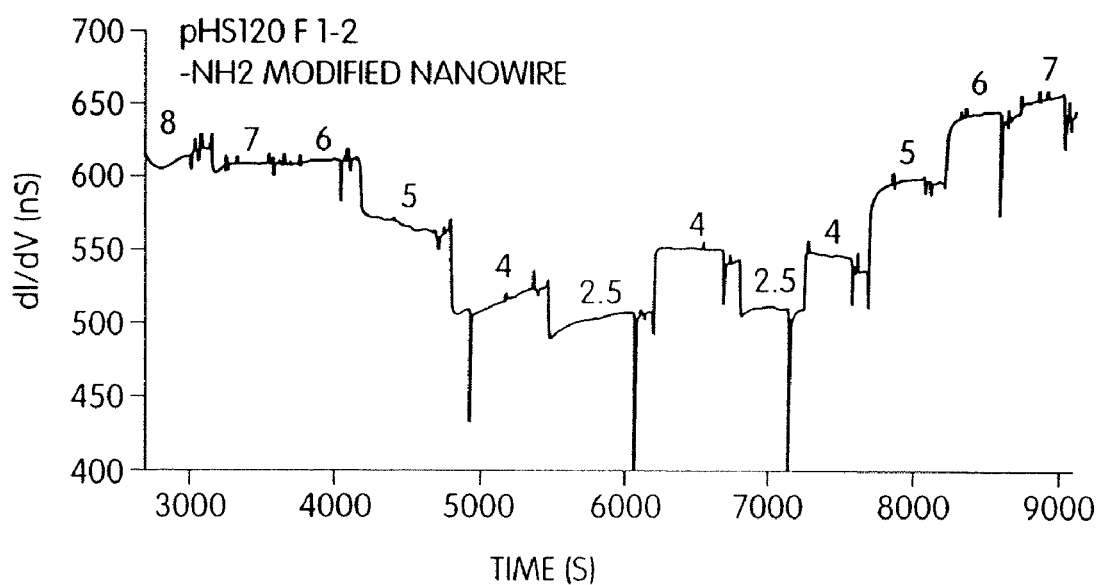
FIG. 5b shows conductance versus pH for a single silicon nanowire that has been modified to expose amine groups at the surface.
Figure 6:
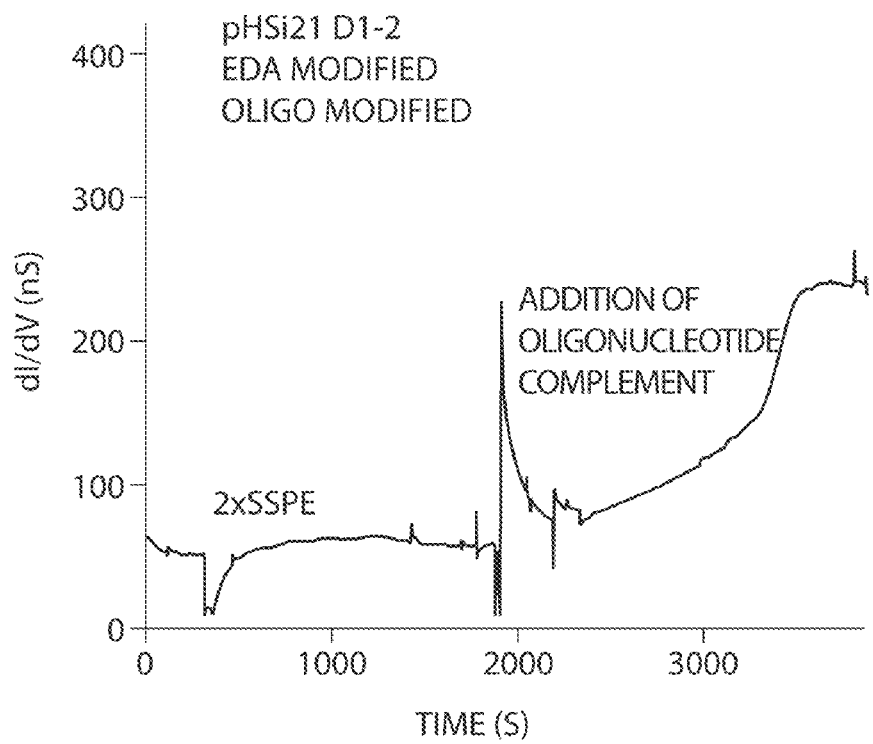
FIG. 6 shows conductance versus time for a silicon nanowire with a surface modified with oligonucleotide agents.

FIGS. 5a and 5b show the conductance for a single silicon nanowire, native and coated, respectively, as a function of pH. As seen in FIG. 4, the conductance of the silicon nanowire changes from 7 to 2.5 when the sample is changed. The silicon nanowire of FIG. 4 has been modified to expose amine groups at the surface of the nanowire. FIG. 5 shows a change in response to pH when compared to the response in FIG. 4. The modified nanowire of FIG. 5 shows a response to milder conditions such as, for example, those present in physiological conditions in blood.

FIG. 6 shows the conductance for a silicon nanowire having a surface modified with an oligonucleotide agent reaction entity. The conductance changes dramatically where the complementary oligonucleotide analyte binds to the attached oligonucleotide agent.

Figure 8A:
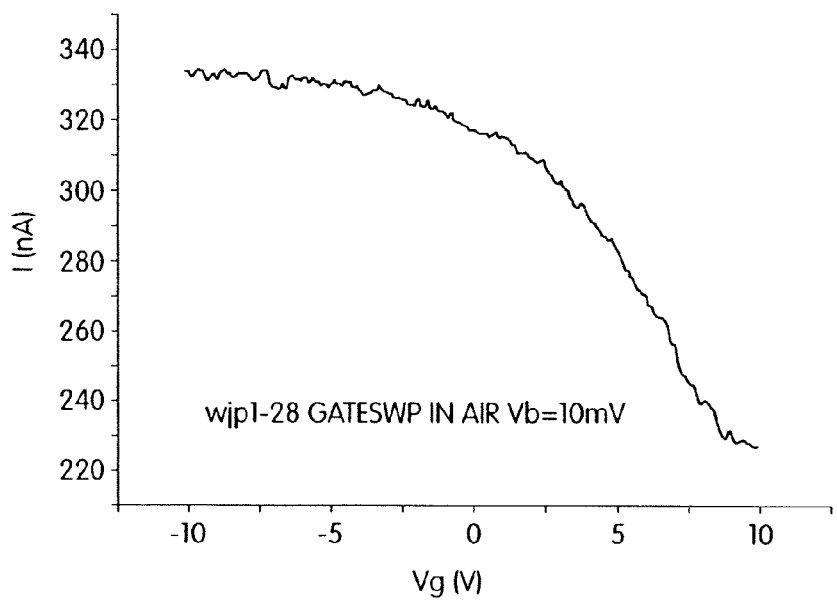
FIG. 8a shows current-voltage (I-V) measurements for a single-walled carbon nanotube device in air.
Figure 8B:
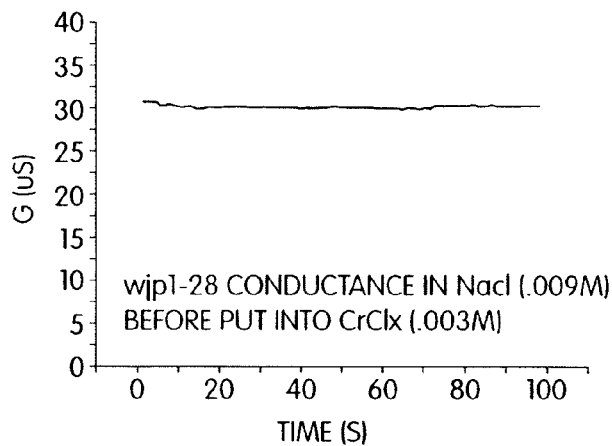
FIG. 8b shows current-voltage (I-V) measurements for the single-walled carbon nanotube device of FIG. 8a in NaCl.
Figure 8C:
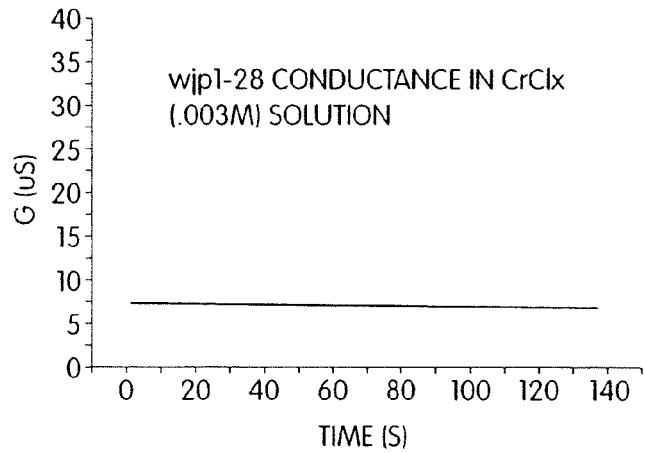
FIG. 8c shows current-voltage (I-V) measurements for a single-walled carbon nanotube device of FIG. 8b in CrClx.

FIG. 8a shows the change in the electrostatic environment with change in gate voltage for a single-walled nanotube. FIGS. 8b and c, show the change in conductance induced by the presence of NaCL and CrClx of a single-walled carbon nanotube.

Figure 9A:
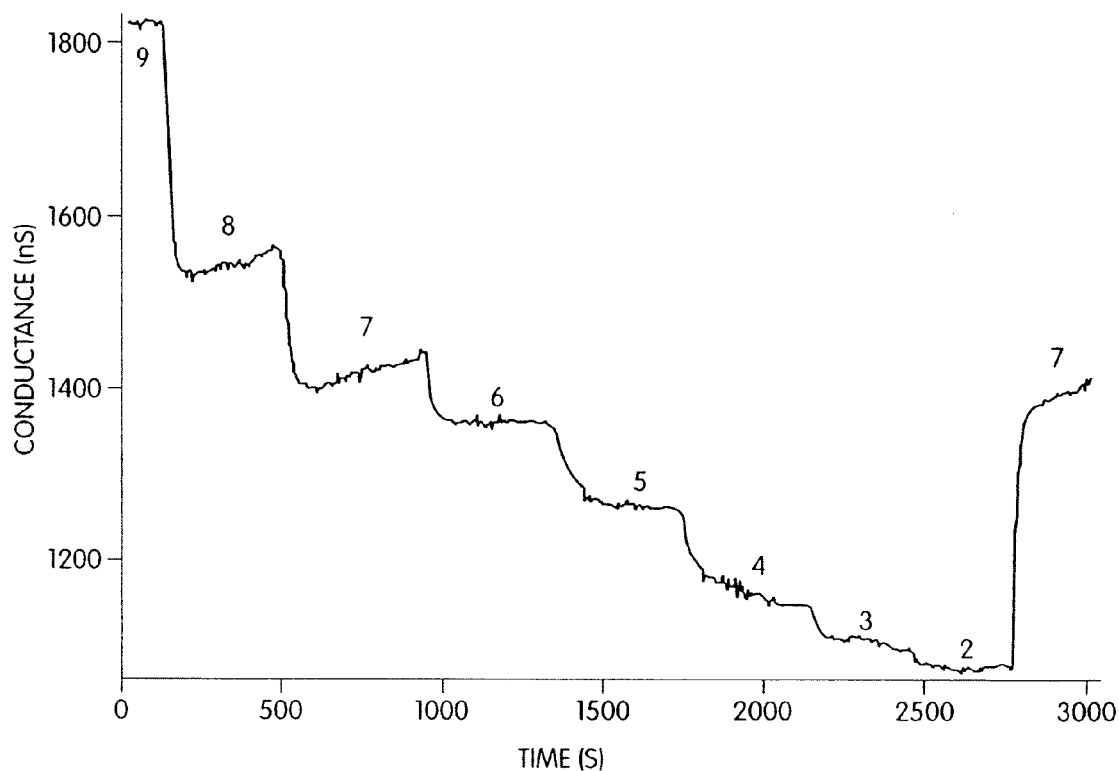
FIG. 9a shows the conductance of nanosensors with hydroxyl surface groups when exposed to pH levels from 2 to 9.
Figure 9B:
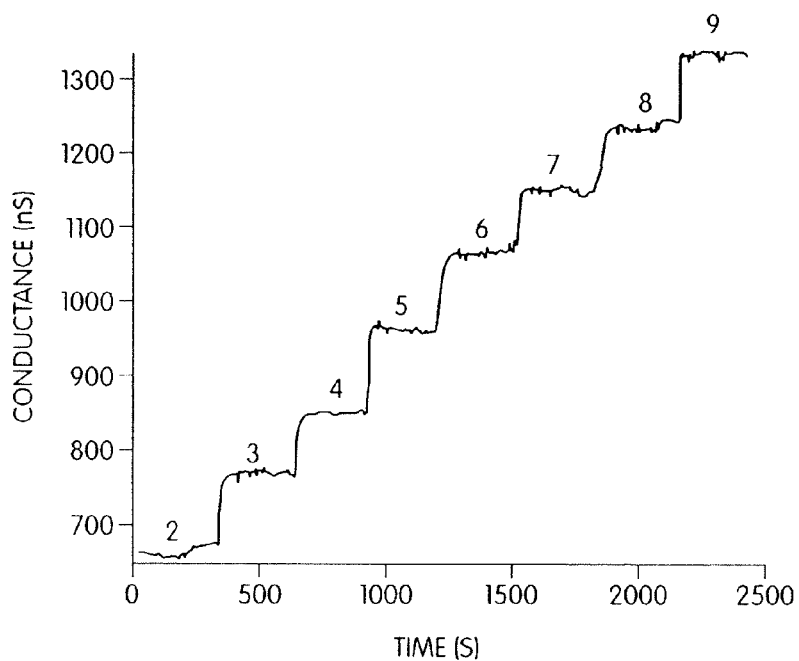
FIG. 9b shows the conductance of nanosensors modified with amine groups when exposed to pH levels from 2 to 9.
Figure 9C:
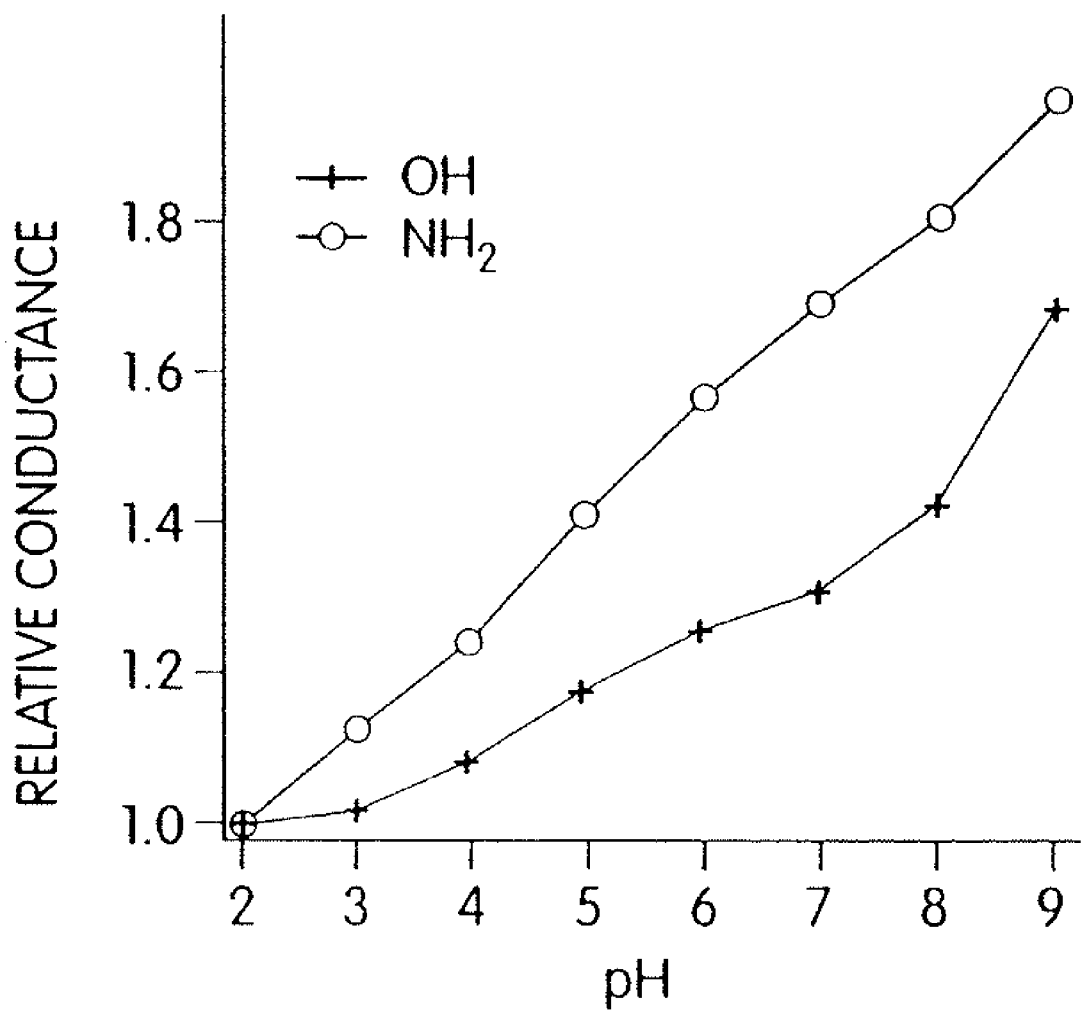
FIG. 9c show the relative conductance of the nanosensors with changes in pH levels.

FIG. 9a shows the change in conductance as nanosensors with hydroxyl surface groups are exposed to pH levels from 2 to 9. FIG. 9b shows the change in conductance as nanosensors modified with amine groups are exposed to pH levels from 2 to 9. FIG. 9c show the relative conductance of the nanosensors with changes in pH levels. The results showed a linear response in a wide range of pH, which clearly demonstrated the device is suitable for measuring or monitoring pH conditions of a physiological fluid.

Figure 10A:
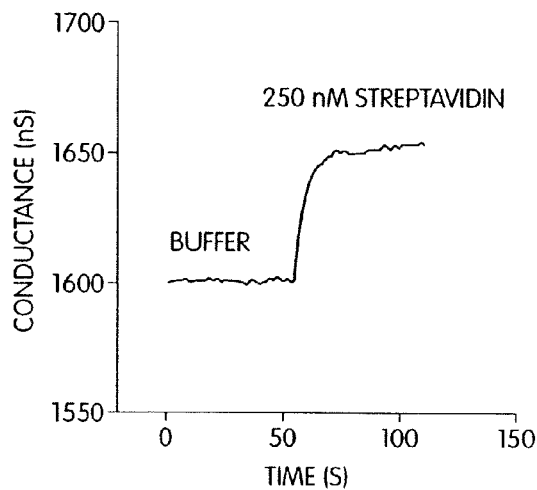
FIG. 10a shows the conductance of a SiNW modified with BSA Biotin, as it is exposed first to a blank buffer solution, and then to a solution containing 250 nM Streptavidin.
Figure 10B:
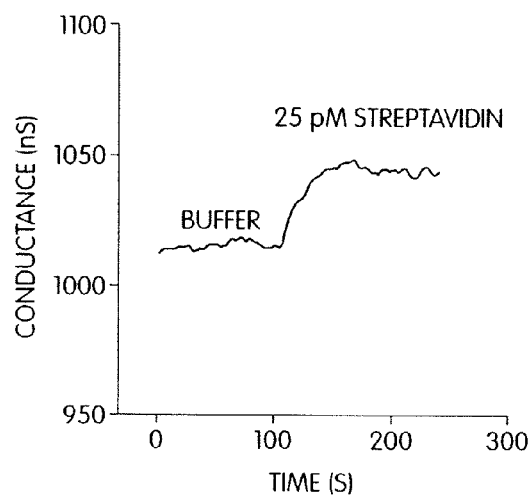
FIG. 10b shows the conductance of a SiNW modified with BSA Biotin, as it is exposed first to a blank buffer solution, and then to a solution containing 25 pM Streptavidin.
Figure 10C:
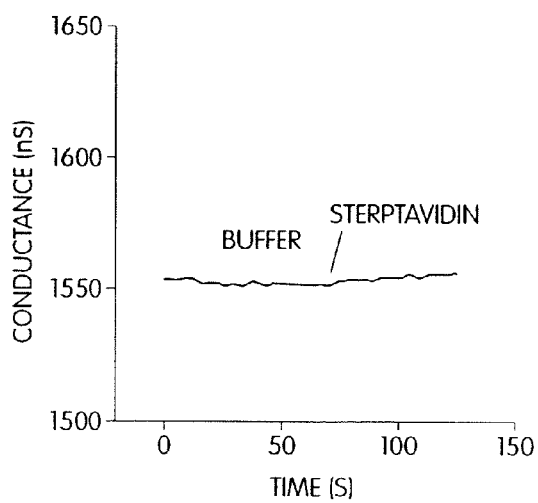
FIG. 10c shows the conductance of a bare SiNW as it is exposed first to a blank buffer solution, and then to a solution containing Streptavidin.
Figure 10D:
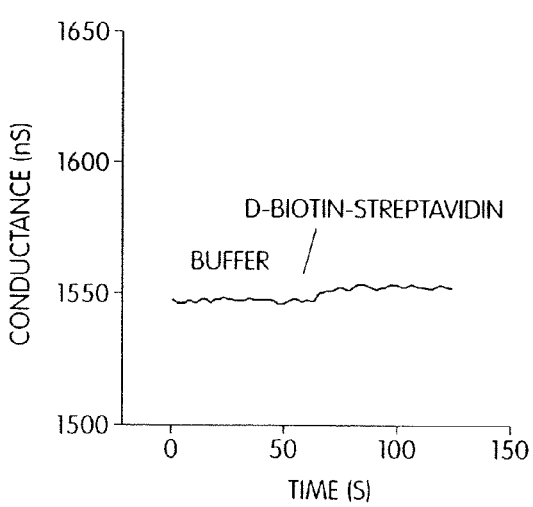
FIG. 10d shows the conductance of a SiNW modified with BSA Biotin, as it is exposed to a buffer solution, and then to a solution containing d-biotin Streptavidin.
Figure 10E:
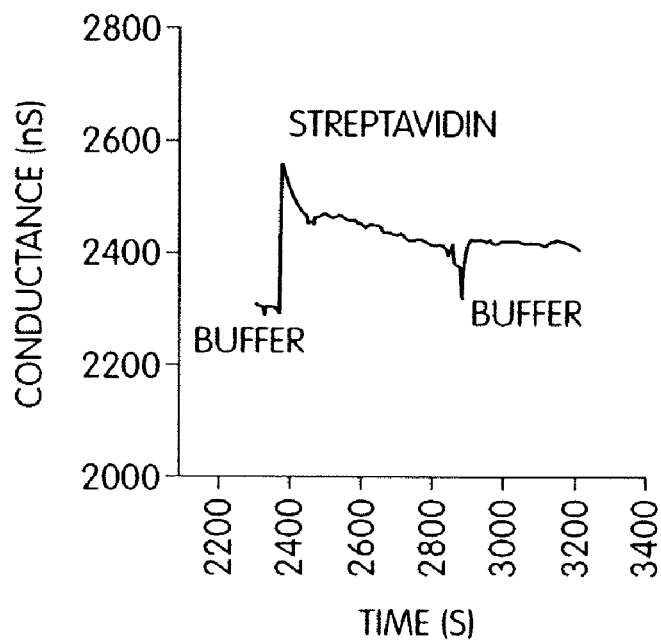
FIG. 10e shows the conductance of a Biotin modified nanosensor exposed to a blank buffer solution, then to a solution containing Streptavidin, and then again to a blank buffer solution.
Figure 10F:
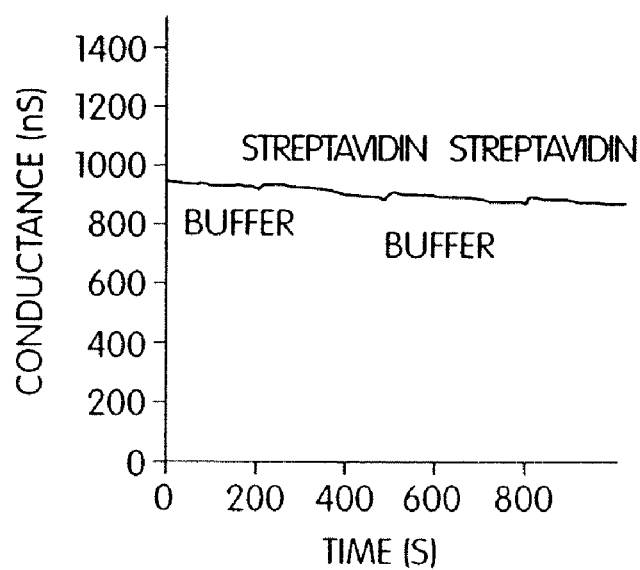
FIG. 10f shows the conductance of a bare SiNW as it is alternately exposed to a buffer solution and a solution containing streptavidin.

FIG. 10a shows an increase in conductance of a silicon nanowire(SiNW) modified with a reaction entity BSA Biotin, as it is exposed first to a blank buffer solution, and then to a solution containing an analyte, 250 nM Streptavidin. FIG. 10b shows an increase in conductance of a SiNW modified with BSA Biotin, as it is exposed first to a blank buffer solution, and then to a solution containing 25 pM Streptavidin. FIG. 10c shows no change in conductance of a bare SiNW as it is exposed first to a blank buffer solution, and then to a solution containing Streptavidin. FIG. 10d shows the conductance of a SiNW modified with BSA Biotin, as it is exposed to a buffer solution, and then to a solution containing d-biotin Streptavidin. FIG. 10e shows the change in conductance of a Biotin modified nanosensor exposed to a blank buffer solution, then to a solution containing Streptavidin, and then again to a blank buffer solution. Replacing Streptavidin with the blank buffer does not change the conductance, indicating that the Streptavidin has irreversibly bound to the BSA Biotin modified nanosensor. FIG. 10f shows no change in conductance of a bare SiNW as it is alternately exposed to a buffer solution and a solution containing streptavidin. These results demonstrate the nanowire sensor is suitable for specific detection of bio-markers at very high sensitivity.

Figure 11A:
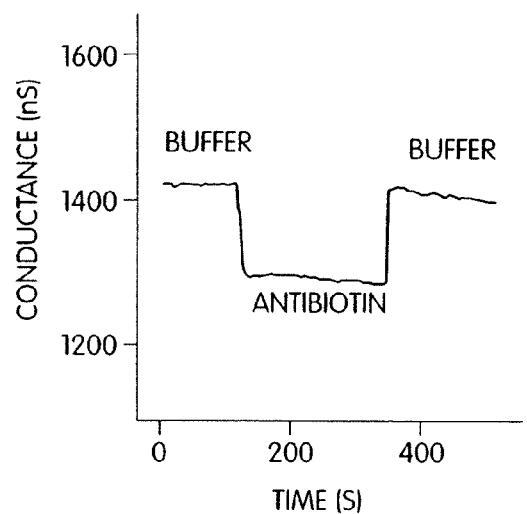
FIG. 11a shows the conductance of a BSA-Biotin modified SiNW as it is exposed first to a blank buffer solution, then to a solution containing Antibiotin.
Figure 11B:
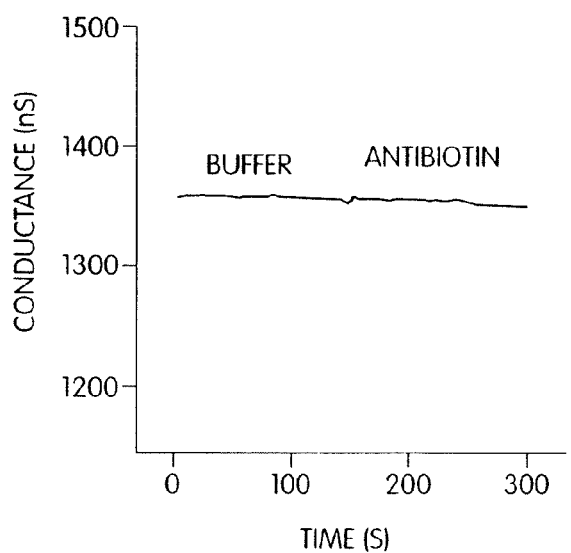
FIG. 11b shows the conductance of a bare SiNW during contact with a buffer solution and then a solution containing Antibiotin.
Figure 11C:
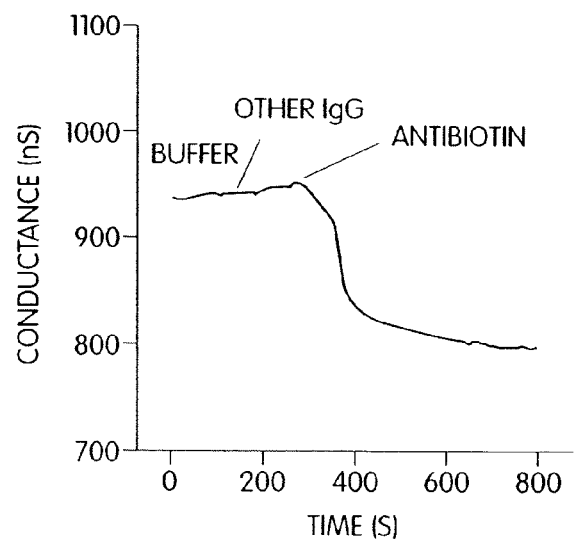
FIG. 11c shows the conductance of a BSA-Biotin modified SiNW during exposure to a buffer, other IgG type antibodies, and then Antibiotin.

FIG. 11a shows a decrease in conductance of a BSA-Biotin modified SiNW as it is exposed first to a blank buffer solution, then to a solution containing antibiotin. The conductance then increases upon replacing the solution containing antibiotin with a blank buffer solution, and then again decreases upon exposing the nanosensor to a solution containing antibiotin. FIG. 11a indicates a reversible binding between biotin and antibiotin. FIG. 11b shows the conductance of a bare SiNW during contact with a buffer solution and then a solution containing antibiotin. FIG. 11c shows the change in conductance of a BSA-Biotin modified SiNW during exposure to a buffer, other IgG type antibodies, and then antibiotin, an IgG1 type antibody to biotin. FIG. 11c indicates that the BSA biotin modified SiNW detects the presence of antibiotin, without being hindered by the presence of other IgG type antibodies. These results demonstrate the potential of the nanowire sensor for dynamic bio-marker monitoring under a real physiological condition.

Figure 12A:
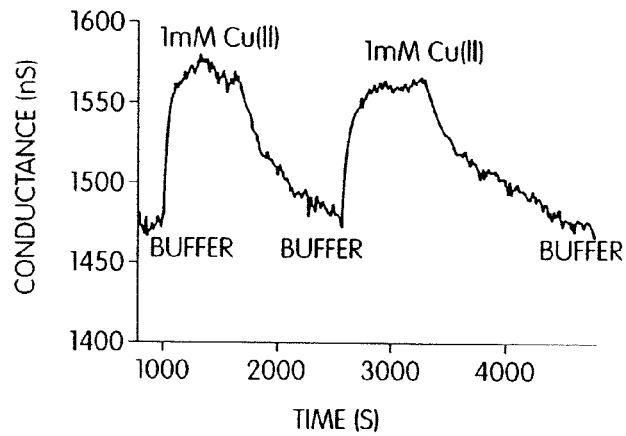
FIG. 12a shows the conductance of an amine modified SiNW when alternately exposed to a blank buffer solution and a solution containing 1 mM Cu(II).
Figure 12B:
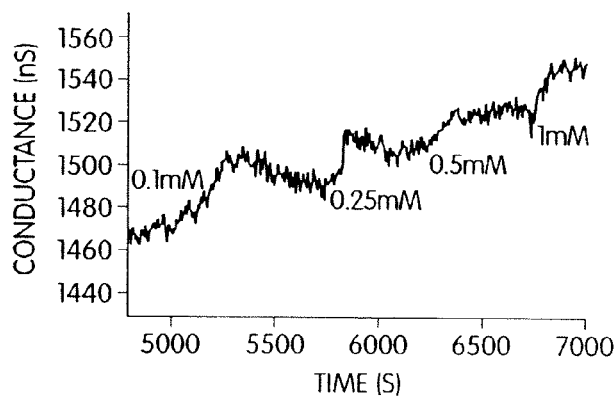
FIG. 12b shows the conductance of the amine modified SiNW is exposed to concentrations of Cu(II) from 0.1 mM to 1 mM.
Figure 12C:
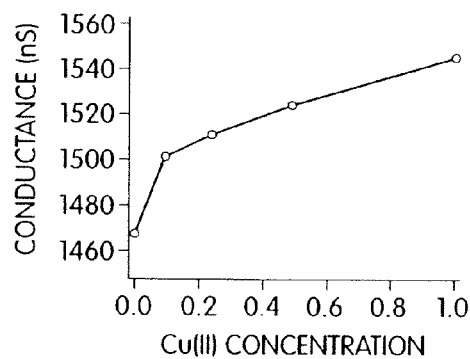
FIG. 12c shows the conductance verses Cu(II) concentration.
Figure 12D:
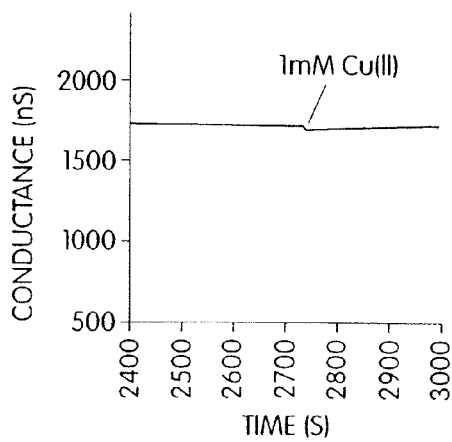
FIG. 12d shows conductance of an unmodified SiNW when exposed first to a blank buffer solution and then to 1 mM Cu(II).
Figure 12E:
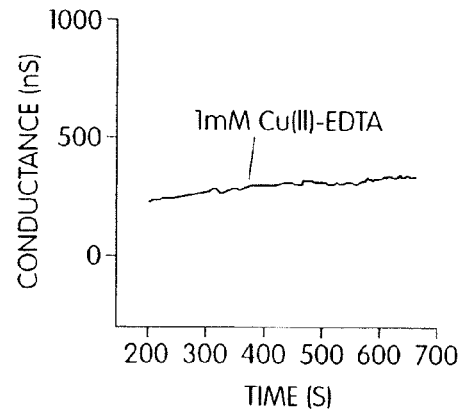
FIG. 12e shows conductance of an amine-modified SiNW when exposed first to a blank buffer solution and then to 1 mM Cu(II)-EDTA.

Amine modified SiNW may also detect the presence of metal ions. FIG. 12a shows the change in conductance of an amine modified SiNW when alternately exposed to a blank buffer solution and a solution containing 1 mM Cu(II). FIG. 12b shows the increases in conductance as the amine modified SiNW is exposed to concentrations of Cu(II) from 0.1 mM to 1 mM. FIG. 12c shows the increase in conductance verses Cu(II) concentration. FIG. 12d shows no change in conductance of an unmodified SiNW when exposed first to a blank buffer solution and then to 1 mM Cu(II). FIG. 12e shows no change in the conductance of an amine modified SiNW when exposed first to a blank buffer solution and then to 1 mM Cu(II)-EDTA, wherein the EDTA interferes with the ability of Cu(II) to bind to the modified SiNW. These results demonstrate the potential of the nanowire sensor for use in inorganic chemical analysis.

Figure 13A:
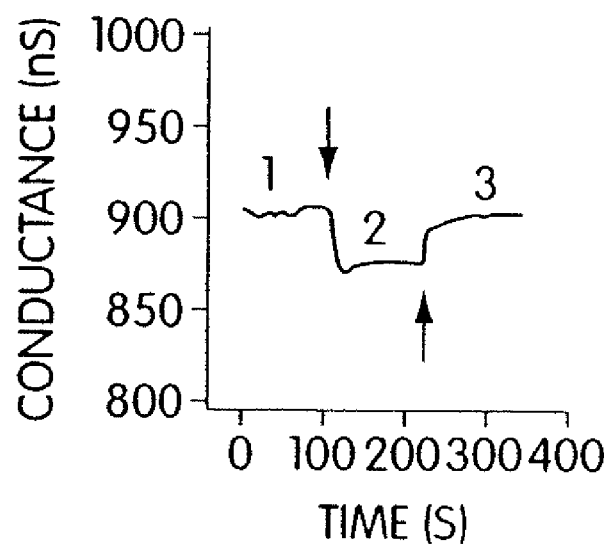
FIG. 13a shows the conductance of a calmodulin-modified silicon nanowire exposed to a buffer solution and then to a solution containing calcium ions.
Figure 13B:
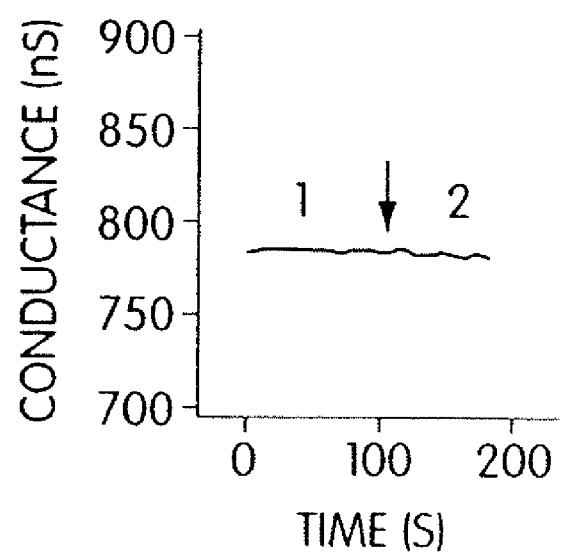
FIG. 13b shows the conductance of a bare silicon nanowire exposed to a buffer solution and then to a solution containing calcium ions.

FIG. 13a shows the conductance of a silicon nanowire modified with calmodulin, a calcium binding protein. In FIG. 13a, region 1 shows the conductance of the calmodulin modified silicon when exposed to a blank buffer solution. Region 2 shows the drop in conductance of the same nanowire when exposed to a solution containing calcium ions noted in FIG. 3 with a downward arrow. Region 3 shows the increase in conductance of the same nanowire is again contacted with a blank buffer solution, indicated with an upward arrow. The subsequent return of conductance to its original level indicates that the calcium ion is reversible bound to the calmodulin modified nanowire. FIG. 13b shows no change in conductance of an unmodified nanowire when exposed first to a blank buffer solution, and then to a solution containing calcium ions.

As indicated by the disclosure above, in one embodiment, the invention provides a nanoscale electrically based sensor for determining the presence or absence of analytes suspected of being present in a sample. The nanoscale provides greater sensitivity in detection than that provided by macroscale sensors. Moreover, the sample size used in nanoscale sensors is less than or equal to about 10 microliters, preferably less than or equal to about 1 microliter, and more preferably less than or equal to about 0.1 microliter. The sample size may be as small as about 10 nanoliters or less. The nanoscale sensor also allows for unique accessibility to biological species and may be used both in vivo and in vitro applications. When used in vivo, the nanoscale sensor and corresponding method result in a minimally invasive procedure.

Figure 14A:
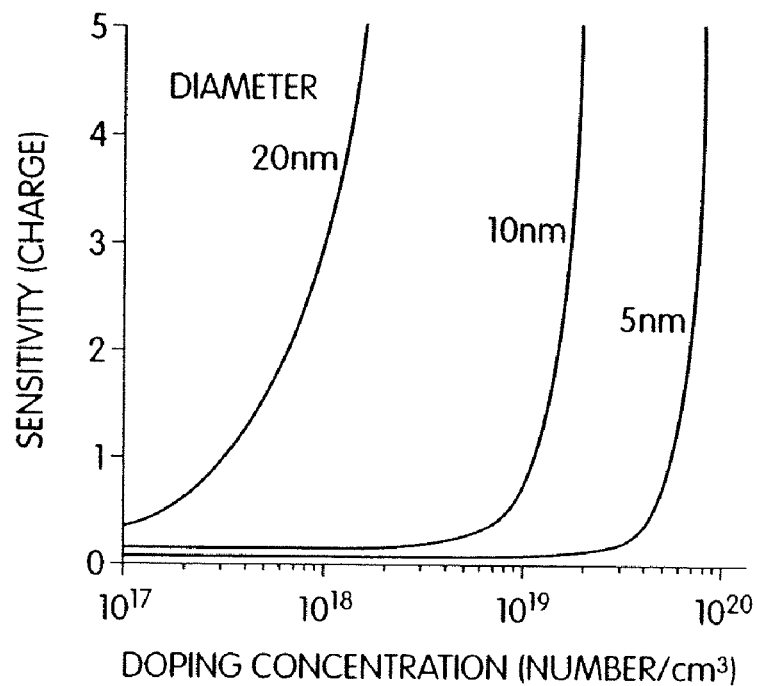
FIG. 14a shows a calculation of sensitivity for detecting up to 5 charges compared with doping concentration and nanowire diameter.
Figure 14B:
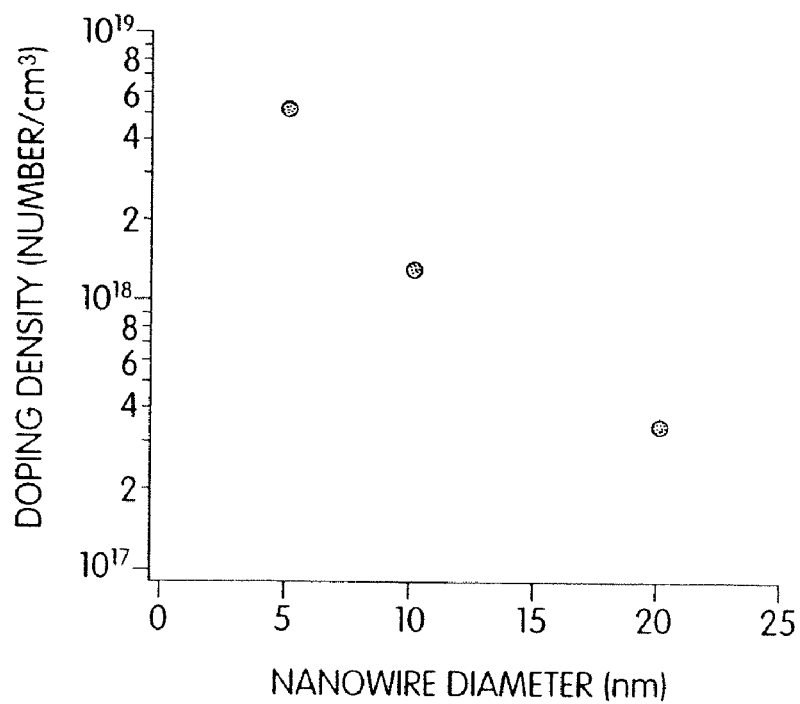
FIG. 14b shows a calculation of the threshold doping density compared to nanowire diameter for detecting a single charge.

FIG. 14a shows a calculation of sensitivity for detecting up to 5 charges compared to the doping concentration and nanowire diameter. As indicated, the sensitivity of the nanowire may be controlled by changing the doping concentration or by controlling the diameter of the nanowire. For example, increasing the doping concentration of a nanowire increases the ability of the nanowire to detect more charges. Also, a 20 nm wire requires less doping than a 5 nm nanowire for detecting the same number of charges. FIG. 14b shows a calculation of a threshold doping density for detecting a single charge compared to the diameter of a nanowire. Again, a 20 nm nanowire requires less doping than a 5 nm nanowire to detect a single charge.

Figure 15A:
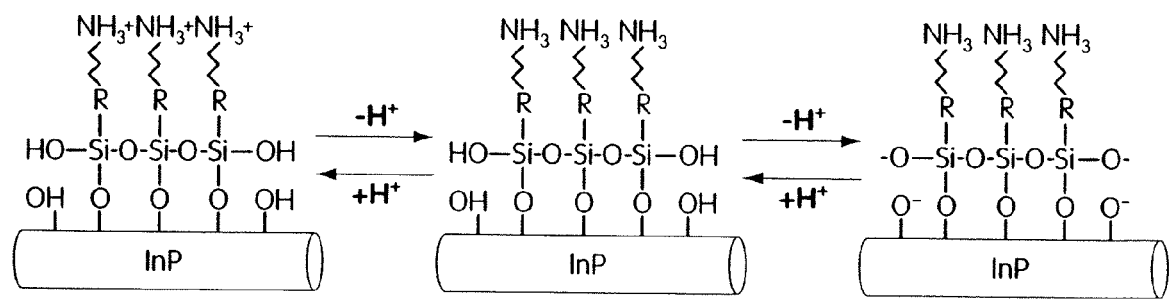
FIG. 15 is a schematic view of an InP nanowire.
FIG. 15b shows the change in luminescence of a nanowire of FIG. 15a over time as pH varies.
Figure 15B:
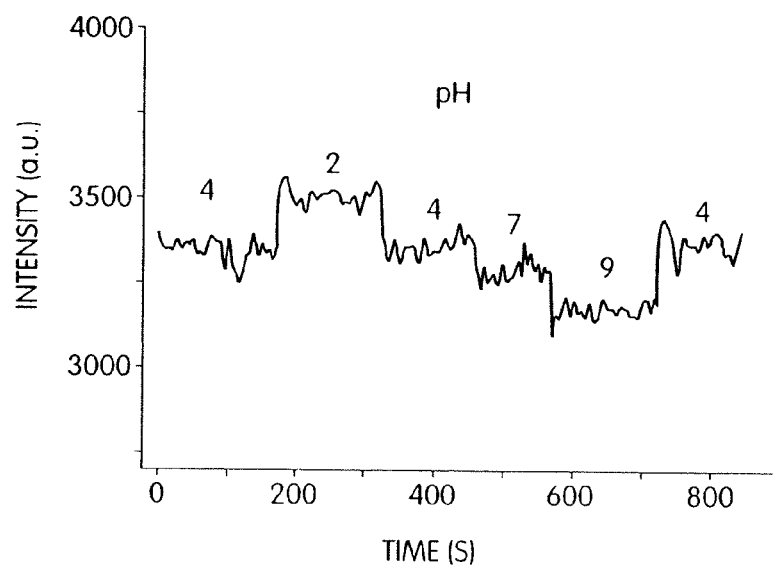

FIG. 15 a shows a schematic view of an InP nanowire. The nanowire may be homogeneous, or may comprise discrete segments of n and p type dopants. FIG. 15b shows the change in luminescence of the nanowire of 15a over time as pH is varied. As indicated, the intensity of the light emission of a nanowire changes relative to the level of binding. As the pH increases, the light intensity drops, and as the pH decreases, the light intensity increases. One embodiment of the invention contemplates individually addressed light signal detection by sweeping through each electrode in a microarray. Another embodiment of the invention contemplates a two signal detector, such as, an optical sensor combined with an electrical detector.

Figure 16A:
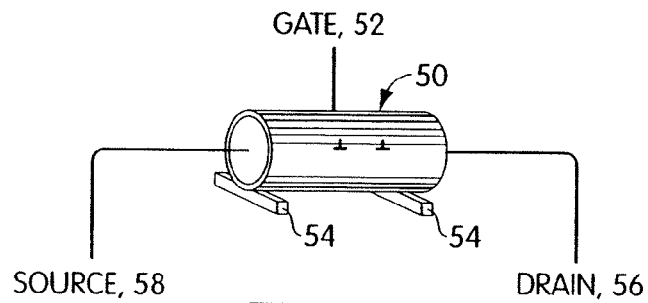
FIG. 16a depicts one embodiment of a nanowire sensor, specifically a chemical or ligand-gated Field Effects Transistor (FET).

FIG. 16a depicts one embodiment of a nanowire sensor. As show in FIG. 16a, the nanowire sensor of the invention comprises a single molecule of doped silicon 50. The doped silicon is shaped as a tube, and the doping can be n-doped or p-doped. Either way, the doped silicon nanowire forms a high resistance semiconductor material across which a voltage may be applied. The exterior surface and the interior surface of the tube will have an oxide formed thereon and the surface of the tube can act as the gate 52 of an FET device and the electrical contacts at either end of the tube allow the tube ends to acts as the drain 56 and the source 58. In the depicted embodiment the device is symmetric and either end of the device may be considered the drain or the source. For purpose of illustration, the nanowire of FIG. 16a defines the left-hand side as the source and the right hand side as the drain. FIG. 16a also show that the nanowire device is disposed upon and electrically connected to two conductor elements 54.

Figure 16B:
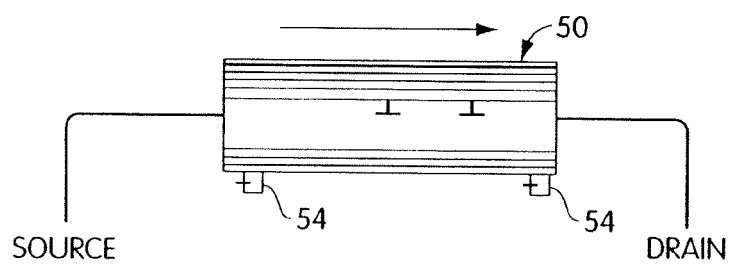

FIGS. 16a and 16b illustrate an example of a chemical/or ligand-gated Field Effects Transistor (FET). FETs are well known in the art of electronics. Briefly, a FET is a 3-terminal device in which a conductor between 2 electrodes, one connected to the drain and one connected to the source, depends on the availability of charge carriers in a channel between the source and drain. FETs are described in more detail in *The Art of Electronics, Second Edition* by Paul Horowitz and Winfield Hill, Cambridge University Press, 1989, pp. 113-174, the entire contents of which is hereby incorporated by reference. This availability of charge carriers is controlled by a voltage applied to a third "control electrode" also know as the gate electrode. The conduction in the channel is controlled by a voltage applied to the gate electrode which produces an electric field across the channel. The device of FIGS. 16a and 16b may be considered a chemical or ligand-FET because the chemical or ligand provides the voltage at the gate which produced the electric field which changes the conductivity of the channel. This change in conductivity in the channel effects the flow of current through the channel. For this reason, a FET is often referred to as a transconductant device in which a voltage on the gate controls the current through the channel through the source and the drain. The gate of a FET is insulated from the conduction channel, for example, using a semi conductor junction such in a junction FET (JFET) or using an oxide insulator such as in a metal oxide semiconductor FET (MOSFET). Thus, in Figures A and B, the SIO2 exterior surface of the nanowire sensor may serve as the gate insulation for the gate.

In application, the nanowire device illustrated in Figure A provides an FET device that may be contacted with a sample or disposed within the path of a sample flow. Elements of interest within the sample can contact the surface of the nanowire device and, under certain conditions, bind or otherwise adhere to the surface.

To this end the exterior surface of the device may have reaction entities, e.g., binding partners that are specific for a moiety of interest. The binding partners will attract the moieties or bind to the moieties so that moieties of interest within the sample will adhere and bind to the exterior surface of the nanowire device. An example of this is shown in FIG. 16c where there is depicted a moiety of interest 60 (not drawn to scale) being bound to the surface of the nanowire device.

Figure 16C:
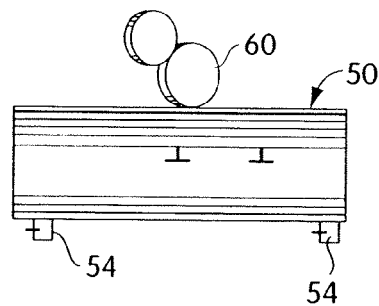
FIG. 16c illustrates the nanowire of FIG. 16a with moieties at the surface.
Figure 16D:
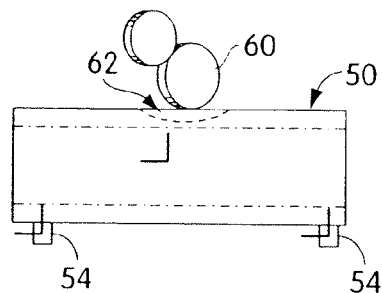
FIG. 16d illustrates the nanowire of FIG. 16c with a depletion region.

Also shown, with reference to FIG. 16c, that as the moieties build up, a depletion region 62 is created within the nanowire device that limits the current passing through the wire. The depletion region can be depleted of holes or electrons, depending upon the type of channel. This is shown schematically in FIG. 16d below. The moiety has a charge that can lead to a voltage difference across the gate/drain junction.

A nanoscale sensor of the present invention can collect real time data. The real time data may be used, for example, to monitor the reaction rate of a specific chemical or biological reaction. Physiological conditions or drug concentrations present in vivo may also produce a real time signal that may be used to control a drug delivery system. For example, the present invention includes, in one aspect, an integrated system, comprising a nanowire detector, a reader and a computer controlled response system. In this example, the nanowire detects a change in the equilibrium of an analyte in the sample, feeding a signal to the computer controlled response system causing it to withhold or release a chemical or drug. This is particularly useful as an implantable drug or chemical delivery system because of its small size and low energy requirements. Those of ordinary skill in the art are well aware of the parameters and requirements for constructing implantable devices, readers, and computer-controlled response systems suitable for use in connection with the present invention. That is, the knowledge of those of ordinary skill in the art, coupled with the disclosure herein of nanowires as sensors, enables implantable devices, real-time measurement devices, integrated systems, and the like. Such systems can be made capable of monitoring one, or a plurality of physiological characteristics individually or simultaneously. Such physiological characteristics can include, for example, oxygen concentration, carbon dioxide concentration, glucose level, concentration of a particular drug, concentration of a particular drug by-product, or the like. Integrated physiological devices can be constructed to carry out a function depending upon a condition sensed by a sensor of the invention. For example, a nanowire sensor of the invention can sense glucose level and, based upon the determined glucose level can cause the release of insulin into a subject through an appropriate controller mechanism.

In another embodiment, the article may comprise a cassette comprising a sample exposure region and a nanowire. The detection of an analyte in a sample in the sample exposure region may occur while the cassette is disconnected to a detector apparatus, allowing samples to be gathered at one site, and detected at another. The cassette may be operatively connectable to a detector apparatus able to determine a property associated with the nanowire. As used herein, a device is "operatively connectable" when it has the ability to attach and interact with another apparatus.

In another embodiment, one or more nanowires may be positioned in a microfluidic channel. One or more different nanowires may cross the same microchannel at different positions to detect a different analyte or to measure flow rate of the same analyte. In another embodiment, one or more nanowires positioned in a microfluidic channel may form one of a plurality of analytic elements in a micro needle probe or a dip and read probe. The micro needle probe is implantable and capable of detecting several analytes simultaneously in real time. In another embodiment, one or more nanowires positioned in a microfluidic channel may form one of the analytic elements in a microarray for a cassette or a lab on a chip device. Those skilled in the art would know such cassette or lab on a chip device will be in particular suitable for high throughout chemical analysis and combinational drug discovery. Moreover, the associated method of using the nanoscale sensor is fast and simple, in that it does not require labeling as in other sensing techniques. The ability to include multiple nanowires in one nanoscale sensor, also allows for the simultaneous detection of different analytes suspected of being present in a single sample. For example, a nanoscale pH sensor may include a plurality of nanoscale wires that each detect different pH levels, or a nanoscale oligo sensor with multiple nanoscale wires may be used to detect multiple sequences, or combination of sequences.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. An article comprising: a semiconductor nanowire and a catalyst material deposited on the semiconductor nanowire which is capable of catalyzing a reaction with an analyte which comes into contact with the nanowire.

2. The article as in claim 1, wherein the semiconductor nanowire is a silicon nanowire.

3. The article as in claim 1, wherein the nanowire has a diameter ranging from 0.5 nm to 200 nm.

4. A method comprising providing a semiconductor nanowire having a catalyst material deposited thereon and contacting the nanowire with a sample having a volume of less than about 10 microliters and at least one analyte disposed therein, wherein the catalyst material catalyzes a reaction with the analyte in the sample.

5. The method as in claim 4, wherein the semiconductor nanowire is a silicon nanowire.

6. The method as in claim 4, wherein the nanowire has a diameter ranging from 0.5 nm to 200 nm.

7. The method as in claim 4, wherein the analyte comprises a chemical moiety.

8. The method as in claim 7, wherein the chemical moiety is an organic compound.

* * * * *

UNITED STATES PATENT AND TRADEMARK OFFICE
CERTIFICATE OF CORRECTION

PATENT NO. : 7,619,290 B2
APPLICATION NO. : 12/038794
DATED : November 17, 2009
INVENTOR(S) : Charles M. Lieber et al.

Page 1 of 1

It is certified that error appears in the above-identified patent and that said Letters Patent is hereby corrected as shown below:

In the Specification

At Column 1, Lines 15-20, please update the paragraph:
"This invention was made with government support under DBI-98346603 awarded by the National Science Foundation, N00014-00-1-0476 awarded by the Office of Naval Research, and CA091357 awarded by the National Institutes of Health. The government has certain rights in the invention."

To:
--GOVERNMENT SUPPORT
This invention was made with government support under CA091357 awarded by the National Institutes of Health, 9834603 awarded by the National Science Foundation, and N00014-00-1-0476 awarded by the Office of Naval Research. The government has certain rights in the invention.--

Signed and Sealed this
Seventh Day of January, 2025

Derrick Brent
*Acting Director of the United States Patent and Trademark Office*